(12) United States Patent
Dasgupta et al.

(10) Patent No.: US 10,228,355 B2
(45) Date of Patent: Mar. 12, 2019

(54) VOLATILE ELUENT PREPARATION

(71) Applicant: Board of Regents, The University of Texas System, Austin, TX (US)

(72) Inventors: Purnendu K. Dasgupta, Arlington, TX (US); Charles Phillip Shelor, Arlington, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 174 days.

(21) Appl. No.: 15/148,988

(22) Filed: May 6, 2016

(65) Prior Publication Data
US 2017/0322188 A1 Nov. 9, 2017

(51) Int. Cl.
*G01N 30/00* (2006.01)
*G01N 30/34* (2006.01)
*B01D 15/16* (2006.01)
*B01D 15/42* (2006.01)
*G01N 1/40* (2006.01)
(Continued)

(52) U.S. Cl.
CPC .......... *G01N 30/34* (2013.01); *B01D 15/166* (2013.01); *B01D 15/426* (2013.01); *G01N 1/4005* (2013.01); *G01N 30/96* (2013.01); *G01N 2030/027* (2013.01)

(58) Field of Classification Search
CPC .. B01D 15/166; B01D 15/424; B01D 15/426; G01N 30/34; G01N 2030/347; G01N 2030/027
See application file for complete search history.

(56) References Cited

U.S. PATENT DOCUMENTS

| 3,897,213 A | 7/1975 | Stevens et al. |
| 3,920,397 A | 11/1975 | Small et al. |
| 3,925,019 A | 12/1975 | Hamish et al. |
| (Continued) | | |

FOREIGN PATENT DOCUMENTS

| JP | 7-136472 A | 5/1995 |
| WO | WO 2010/068272 A1 | 6/2010 |

OTHER PUBLICATIONS

Articled titled "Gas Permeation in Perflurosulphonated Membranes: Influence of Temperature and Relative Humidity" by Baschettit et al. published in 2012.*

(Continued)

*Primary Examiner* — Blake A Tankersley
(74) *Attorney, Agent, or Firm* — Morgan, Lewis & Bockius LLP

(57) ABSTRACT

There is provided a system for performing a chromatographic separation of an analyte, methods of using the system to separate at least one component of an analyte and an eluent generator of use in the system. An exemplary system comprises: (a) an eluent generator comprising: (i) a housing configured to be pressurizable by gas, comprising an annular void defined by the housing, and a gas inlet for the gas and a gas outlet for the gas in fluid communication with the annular void; (ii) a membrane permeable to the gas defining an eluent flow channel disposed within the annular void, the eluent flow channel having an eluent precursor fluid inlet and an eluent outlet; (iii) a source of gas in fluidic communication with the gas inlet; (iv) a source of the eluent precursor fluid; and (b) a chromatography column disposed downstream of and in fluidic communication with the eluent outlet.

30 Claims, 47 Drawing Sheets

(51) Int. Cl.
*G01N 30/96* (2006.01)
*G01N 30/02* (2006.01)

(56) References Cited

U.S. PATENT DOCUMENTS

| | | |
|---|---|---|
| 3,926,559 A | 12/1975 | Stevens |
| 4,403,039 A | 9/1983 | Ban et al. |
| 4,459,357 A | 7/1984 | Jansen et al. |
| 4,474,664 A | 10/1984 | Stevens et al. |
| 4,500,430 A | 2/1985 | Dasgupta |
| 4,647,380 A | 3/1987 | Dasgupta |
| 4,751,004 A | 6/1988 | Stevens et al. |
| 4,927,567 A | 5/1990 | Rudick |
| 4,999,098 A | 3/1991 | Pohl et al. |
| 5,045,204 A | 9/1991 | Dasgupta et al. |
| 5,565,149 A | 10/1996 | Page et al. |
| 5,623,105 A | 4/1997 | Liston et al. |
| 6,036,921 A | 3/2000 | Small et al. |
| 6,225,129 B1 | 5/2001 | Liu et al. |
| 6,544,484 B1 | 4/2003 | Kaufman et al. |
| 6,568,245 B2 | 5/2003 | Kaufman |
| 6,712,342 B2 | 3/2004 | Bosko |
| 7,306,720 B2 | 12/2007 | Dasgupta et al. |
| 8,647,576 B2 | 2/2014 | Liu et al. |
| 8,808,775 B2 | 8/2014 | Novak et al. |
| 8,844,909 B2 | 9/2014 | Xia |
| 2008/0311672 A1 | 12/2008 | Dasgupta et al. |
| 2016/0041133 A1 | 2/2016 | Pohl et al. |
| 2016/0114264 A1* | 4/2016 | Liu .................... B01D 19/0031 95/46 |
| 2016/0131620 A1* | 5/2016 | Murphy ................. G01N 30/06 250/282 |

OTHER PUBLICATIONS

AZYP, LARIHC Series HPLC Column Operating Instructions, pp. 1-2.
Dionex IonPac AS9-SC and AS9-HC Anion-Exchange Column, Thermo Scientific, pp. 1-6.
Liao, et al., "Permeative Amine Introduction for Very Weak Acid Detection in Ion Chromatography", analytical chemistry, 2016, 88(4), pp. 2198-2204.
Michalski, R., "Application of Ion Chromatography in Clinical Studies and Pharmaceutical Industry", Mini-Rev. med. Chem., 2014, 14, pp. 862-872.
Product Manual "MAbPac™ SCX-10", Thermo Scientific, Jan. 2012, Document No. 065393, pp. 1-30.
Product Manual "IONPAC® CG3 Guard Column (4x 50 mm, P/N 037025) and IONPAC® CS3 Analytical Column (4x 250 mm, P/N 037024)", Thermo Scientific, Nov. 7, 2002, Document No. 032654, pp. 1-17.
Product Manual "IonPac® ICE-AS6", Thermo Scientific/Dionex, Aug. 29, 2005, Document No. 034961, pp. 1-47.
Product Manual "Anion-ICE MicroMembrane™ Suppressor 300, AMMS® ICE 300", Thermo Scientific/Dionex, Aug. 29, 2005, Document No. 032661, pp. 1-15.
Strong, et al. "Electrodialytic Eluent Production and Gradient Generation in Ion Chromatography", Analytical Chemistry, 1991, 63, pp. 480-486.
Ullah, Rahmat S.M., et al. "Asymmetric Membrane Fiber-Based Carbon Dioxide Removal Devices for Ion Chromatography", Anal. Chem., 2004, 76, pp. 7084-7093.
Vanatta, L. E. "Application of ion chromatography in the semiconductor industry", TrAC, Trends Anal. Chem, 2001, 20, pp. 336-345.
Edmund J. Bishop, et al. "On-line membrane preconcentration for continuous monitoring of trace pharmaceuticals", Journal of Pharmaceutical and Biomedical Analysis 37 (2005), pp. 81-86.

* cited by examiner 10 mM CO₂ with KOH EG

CO₂ INTO 10 mM KOH Eluent

FIG. 24A

Knowns
Flow Rate (F), pH, Ionic Strength (I),
$CO_2$ permeation rate ($\beta_{CO2}$),
$NH_3$ Permeation Rate ($\beta_{NH3}$)

Adjustables
$CO_2$ Pressure,
$NH_3$ Pressure

Constants
$K_w = [H^+][OH^-] = 1*10^{-14}$
$Ka_{NH4+} = [H^+][NH_3]/[NH_4^+] = 5.62341*10^{-10}$
$Ka_{H2CO3} = [H^+][HCO_3^-]/[CO_2] = 4.2658*10^{-7}$
$Ka_{HCO3-} = [H^+][CO_3^{2-}]/[HCO_3^-] = 4.67735*10^{-11}$

*Includes Hydration Equilibrium*
*Pressure Dependent*

Starting Equations
$Q = ([H^+]^2 + [H^+]Ka_{H2CO3} + Ka_{H2CO3}Ka_{HCO3-})^{-1}$
$[CO_2] = C_{Total}Q[H^+]^2$
$[HCO_3^-] = C_{Total}Q[H^+]Ka_{H2CO3}$
$[CO_3^{2-}] = C_{Total}QKa_{HCO3-}Ka_{H2CO3}$ $I = 0.5 * ([H^+] + [NH_4^+] + [OH^-] + [HCO_3^-] + 4*[CO_3^{2-}])$

*Charge Balance*
$[H^+] + [NH_4^+] = [OH^-] + [HCO_3^-] + 2*[CO_3^{2-}]$

*$NH_4^+$ can be replaced with any cation!*

$[NH_4^+] = [OH^-] + [HCO_3^-] + 2*[CO_3^{2-}] - [H^+]$

*Substitute Charge Balance into Ionic Strength*

$I = 0.5 * ([H^+] + [NH_4^+] + [OH^-] + [HCO_3^-] + 4*[CO_3^{2-}])$ $I = 0.5 * (2*[OH^-] + 2*[HCO_3^-] + 6*[CO_3^{2-}]) = [OH^-] + [HCO_3^-] + 3*[CO_3^{2-}]$

*Sub in species specific formulas*

$I = K_w/[H^+] + ([H^+]Ka_{H2CO3} + 3*Ka_{H2CO3}Ka_{HCO3-})*Q*C_{Total}$

*Solve for $C_{Total}$*

$(I - K_w/[H^+])/[([H^+]Ka_{H2CO3} + 3*Ka_{H2CO3}Ka_{HCO3-})*Q] = C_{Total}$

*Solve for Desired Pressure*

$P_{CO2} = C_{Total} * F / \beta_{CO2}$

FIG. 24B

$$[NH_4^+] = [OH^-] + [HCO_3^-] + 2*[CO_3^{2-}] - [H^+]$$

*From Charge Balance determine $NH_4^+$ using calculated concentrations*

$$[NH_4^+] = K_w/[H^+] + ([H^+]Ka_{H2CO3} + 2*Ka_{H2CO3}Ka_{HCO3})*Q*C_{Total} - [H^+]$$

*Use $NH_3$ Equilibrium and $NH_4^+$ concentration to determine total N*

$$N_{Total} = NH_4^+ + NH_3 = NH_4^+ + [H^+]Ka_{NH3}/[NH_4^+]$$

*Solve for Desired Pressure*

$$P_{NH3} = N_{Total} * F / \beta_{NH3}$$

FIG. 34

| Protein | Myoglobin | Cytochrome c | Ubiquitin | Lactalbumin | Cytochrome C |
|---|---|---|---|---|---|
| Origin | Equine Skeletal Muscle | Bovine Heart | Bovine Erythrocytes | Bovine Milk | Equine Heart |
| Molecular Weight (kDa) | 16.9 | 12.2 | 8.6 | 14.2 | 12.3 |
| pI | 7.3 | 10.4-10.8 | 6.8 | 4.5 | 10-10.5 |

VOLATILE ELUENT PREPARATION

STATEMENT AS TO RIGHTS TO INVENTIONS MADE UNDER FEDERALLY SPONSORED RESEARCH OR DEVELOPMENT

This invention was made with Government support under Grant Number NSF CHE-1506572 awarded by the National Science Foundation (NSF). The Government has certain rights to this invention.

FIELD OF THE INVENTION

The present invention relates to liquid or ion chromatography and enhanced detection of analytes in analytical and preparative chromatography modes.

BACKGROUND OF THE INVENTION

Human error in preparing chromatographic eluent solutions, as well as contamination of these solutions on storage or during other periods of disuse, limits the formation of eluents of precise composition and the reproducibility of eluent composition from analysis to analysis, adversely affecting the reproducibility of chromatographic analyses. An important and well known example is the preparation of hydroxide eluents for ion chromatography (IC) where $CO_2$ intrusion into the eluent results in carbonate contamination of the hydroxide eluent. The longer an eluent sits idle exposed to ambient air, the more the carbonate concentration increases. Thus, devices and methods for reproducible formation of eluents on an "as needed" basis are needed in liquid and ion chromatography.

A different area of concern is that eluent components essential in the separation process may be detrimental for detection. For example, it is challenging to separate amino acids, peptides, and proteins without any ionic constituents in the eluent. However, when using electrospray ionization mass spectrometry (ESI-MS), the most commonly used detection method today for such separations, the ionic constituents significantly interfere with the analyte measurement.

An electrodialytic membrane based eluent generator was invented to produce high purity reproducible hydroxide eluents on-line, on-demand (Strong, et al. *Anal. Chem.* 1991, 63 (5):480-486). U.S. Pat. No. 5,045,204 discloses an exemplary eluent generator. The device generates a high purity aqueous stream with selected ionic species—either cation (e.g. sodium) or anion (e.g. sulfate) suitable for use as a chromatography eluent. In one embodiment, the eluent generator includes a source channel and a product channel separated by a permselective ion exchange membrane including exchangeable ions of the same charge as the selected ionic species. The membrane allows passage of ions of the same charge as the ionic species but is resistant to transmembrane passage of ions of opposite charge. An electrical potential is applied between the source channel and product channel.

Other exemplary eluent generators are described in U.S. Pat. No. 6,036,921 and U.S. Pat. No. 6,225,129. All above devices are electrolytic devices disclosed as being useful to generate high purity acid and base solutions by using water as the carrier. Using these devices, high purity, contaminant-free acid or base solutions are automatically generated on-line for use as eluents in chromatographic separations. These devices simplify gradient separations that can now be performed using electrical current gradients with minimal delay instead of using a conventional mechanical gradient pump.

Another exemplary eluent generator is described in U.S. Pat. No. 8,647,576. An acid or base is generated in an aqueous solution by the steps of: (a) providing a source of first ions adjacent an aqueous liquid in a first acid or base generation zone, separated by a first barrier (e.g., anion exchange membrane) substantially preventing liquid flow and transporting ions only of the same charge as said first ions, (b) providing a source of second ions of opposite charge adjacent an aqueous liquid in a second acid or base generation zone, separated by a second barrier transporting ions only of the same charge as the second ions, and (c) transporting ions across the first barrier by applying an electrical potential through said first and second zones to generate an acid-containing aqueous solution in one of said first or second zones and a base-containing aqueous solution in the other one which may be combined to form a salt.

In electrolytic eluent generators, concentration may be controlled by simply altering the current applied to the device. In chromatographic separations, it is often necessary to generate gradients where the pH and ionic strength are varied independently or together, with or without an organic solvent included in the gradient. The complexity of the controlled generation of such eluent gradients is not only increased by the number of individual solutions/fluids that must be made/handled, the complexity of such preparation increases with a proportionate toll on reproducibility. The rise of ultrahigh performance chromatography (UPLC), smaller particles sizes, and shorter columns has also seen the need to use high pressure mixing and multiple pumps in order to reduce the gradient delay time. Eluent generators on the high pressure side have the advantage of lower delay times and obviate the need for a mixing chamber. In addition, the widespread use of electrospray ionization mass-spectrometry (MS) has made the demand for very high purity volatile buffers a necessity.

Recently, it was shown that gas permeable membranes can be used for the addition of basic gases into an eluent stream to raise the pH for the conductometric detection of weak acids (Liao, et al., *Anal. Chem.* 2016, 88 (4):2198-2204).

The use of neutral gases and gases derived from organic solvents (e.g., MeOH, $CH_3CN$), ammonia and volatile bases and volatile acids to alter the composition and characteristics of an eluent stream in an eluent generator provides a different and promising addition to the current range of electrolytic eluent generators. If such devices could be configured to produce eluents of predictable and reproducible composition and characteristics in isocratic and gradient formats, this would represent a significant improvement in the field of chromatography and generating eluents for chromatography. The present invention provides such a device, systems incorporating this device and methods of using the device and systems in chromatographic separations.

BRIEF SUMMARY OF THE INVENTION

The present invention provides a solution to a problem long recognized in the field of chromatography, the separation and detection of weakly dissociating acids and bases using basic and acidic eluents generated in a manner that is both precise and reproducible. The invention provides devices, systems and methods for introducing into an eluent precursor and/or an eluent a gas, e.g., $CO_2$, $NH_3$, a gas derived from a volatile acid, a gas derived from a volatile base, or a gas derived from an organic solvent (e.g., MeOH, $CH_3CN$), thereby generating an eluent containing desired components and having a desired composition. The invention provides an array of eluent formats in which acids, bases, aqueous solutions and organic solvents can be combined in pre-selected proportions. In various embodiments, the eluent generated by the eluent generator of the invention is incorporated into a chromatographic system and is utilized in the chromatographic separation of an analyte of interest. Exemplary eluents produced by the eluent generator of the invention (e.g., those containing a gas derived from a volatile acid or a volatile base) promote dissociation of at least one component of the analyte of interest, e.g., an acid or base component, respectively. The dissociated analyte is detectable against a low background of the eluent. In various embodiments, the analyte of interest may be detected variously using a conductivity detector, an evaporative light scattering detector, a charged aerosol detector, and a electrospray ionization mass spectrometer, among others; these detector particularly benefit from an eluent background that contain no ions or dissolved solids.

The intrinsic volatility of the eluent components makes it facile to remove the eluent components after separation, allowing ready detection of analyte components sensitively. In an exemplary embodiment, the detection of the analyte component is a background that contains little more than the background solvent.

An exemplary eluent generator of the invention includes a hollow, gas permeable membrane defining a lumenal eluent fluid flow channel. The membrane, which is essentially impermeable to the liquid eluent precursor and/or eluent, is permeable to the gas, allowing entry of the gas into the lumen of the eluent fluid flow channel where it dissolves in and/or reacts with a component of an eluent precursor fluid or the eluent. The eluent thus formed is of use in performing a chromatographic separation in a chromatography column downstream from the eluent generator.

The removal of volatile components from a flowing stream is described in U.S. Pat. No. 7,306,720 and Ullah et al., *Anal. Chem.* 2004, 76 (23), 7084-7093. A commercially available carbon dioxide removal device (CRD) based on this invention for example comprises of a thin-wall gas-permeable jacketed membrane tube that has a vacuum drawn on the jacket to remove the dissolved $CO_2$. Alternatively a base solution can be used in the jacket to absorb the CO2 permeating out through the membrane. If eluents are made by dissolving gases under pressure, they can be later (after separation is accomplished) by devices like the CRD. Exemplary eluent generators of the instant invention differ from prior eluent generators by adding a pre-determined amount of a gas to an eluent precursor and/or an eluent, which is separated from the gas source by a gas permeable membrane, which is essentially impermeable to the eluent precursor and/or eluent, to form an eluent containing a pre-selected amount of an ion derived from the gas introduced into the eluent.

Additional embodiments, objects and advantages of the invention are apparent from the detailed description set forth herein below.

BRIEF DESCRIPTION OF THE DRAWINGS

FIG. 24A and FIG. 24B are illustrative derivations for programmable pH and ionic strength control. Engasser permeation constants are assumed to be known. Addition of other acid or base species in the influent solution to the Engasser is readily incorporated in this algorithm to calculate gas pressures necessary to achieve a certain pH and/or ionic strength.

In FIG. 25A, $CO_2$ allows buffering at higher pH and higher attainable ionic strength. This makes the separation of tyrosine, phenylalanine, and tryptophan easier than in the present case since these amino acids are highly retained at low pH but rapid transition to higher pH may cause them to elute all at once. While a higher pH is attainable when $CO_2$ is not used and histidine, lysine, and arginine can be eluted earlier, the resolution between histidine and lysine is reduced.

FIG. 34 is a table with information relevant to the 5 proteins separated in FIG. 35 and includes the protein mass and isoelectric point (pI).

DETAILED DESCRIPTION OF THE INVENTION

I. Introduction

Figure 1:
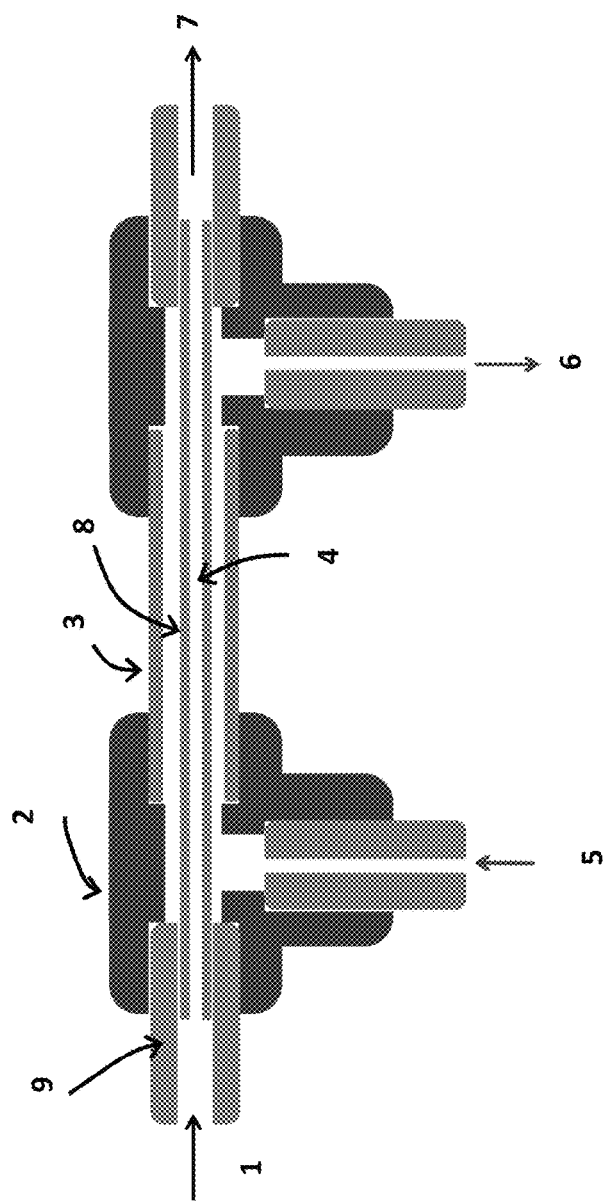
FIG. 1 is the general eluent generator ("Engasser") design for $CO_2$ introduction into an eluent precursor.

Eluents used in high-performance liquid chromatography (HPLC) are produced using a gradient pump and each individual eluent component must be prepared separately before being combined into the gradient.

Gases are typically available in very high purity (99.999+ %). A gas permeable membrane defining an eluent fluid flow channel can serve as an efficient barrier to any nonvolatile material/adventitious particles present while allowing the gas to penetrate the membrane and contact an eluent precursor fluid and/or an eluent disposed within the eluent fluid flow channel. Because the rate of gas introduction (permeation) into the eluent fluid flow channel is dependent on the differential partial pressure of the gas across the membrane, the dissolved gas concentration in the eluent generators of the invention may be altered simply by altering the external pressure of the gas. Using this principle, the present invention provides eluent generators producing eluents including gas-derived components of pre-determined and reproducible concentration(s).

Described herein are the construction, and principles of operation of exemplary eluent generators of the invention, systems incorporating such eluent generators and methods of using such eluent generators and systems in various chromatographic separations relying on diverse separation modalities.

The present invention provides devices and methods of eluent generation using gas permeable membranes for the introduction of neutral, acidic and basic gases to an eluent precursor/eluent form eluents consisting of acids, bases, salts buffers, and/or organic solvents. The present invention is of particular use in forming eluents that are also volatile and hence easily removed under vacuum.

In accordance with the present invention, devices, systems, and methods are provided for generating a high purity aqueous, polar organic, or hydroorganic stream with selected acidic or basic species and suitable for use as a chromatography eluent. In one form, an eluent generator includes an eluent flow channel defined by a gas permeable membrane. The membrane is disposed within a housing, which is substantially impermeable to the gas. The housing is charged with the gas while an eluent precursor solution flows through the eluent flow channel. The gas crosses the membrane in to the eluent precursor or eluent solution, thereby forming the eluent, e.g., an eluent of a predetermined composition. Exemplary gases include $CO_2$, $NH_3$, gases derived from volatile amines, and those derived from volatile acids.

II. Definitions

A "weakly dissociated acid" is an acid analyte with a $pK_a$ of from about 5 to about 10.

A "weakly dissociated base" is a base analyte with a $pK_b$ of from about 5 to about 10.

A "volatile acid" or a "volatile base" refers to the respective species in vapor, neat liquid or solution form.

A "gas permeable membrane" refers to a membrane at least partially permeable to an uncharged molecule. The membrane can be of any useful configuration, including flat, tubular, multi-annular, etc. Exemplary permeable membranes include Teflon AF, and ion exchange membranes. The permeable membrane can be a gas permeable and liquid impermeable membrane (at a given pressure).

An "eluite" refers to a chromatographic solute or analyte.

An "eluent precursor" refers to any liquid capable of dissolving the gas in the Engasser. Exemplary eluent precursors are those liquids generally recognized as chromatographic eluents and includes water, polar organic solvents, hydroorganic mixtures, with or without acids, bases, or salts further added.

The terms "Engasser" and "eluent generator" are used interchangeably herein to refer to an eluent generator of the invention.

An "amorphous fluoropolymer" refers to a family of polymers based on copolymers of 2,2-bistrifluromethyl-4,5-difluro-1,3-dioxole. An exemplary amorphous fluoropolymer is Teflon AF®.

"Dionex IonPac ICE-AS6" is an ion exclusion chromatography column where the resin has two types of ion-exchange groups (sulfonic and carboxylic acid) and hydrophobic groups. The substrate is a 8 micron microporous bead with 8% divinylbenzene crosslinker.

"Dionex MAbPac SCX-10" is a strong cation exchange chromatography column where the resin is a highly cross-linked divinylbenzene media with sulfonic acid groups.

"PSIA" refers to pounds per square inch absolute.

III. Exemplary Embodiments

In various embodiments, the invention provides a system for performing a chromatographic separation of an analyte. The system comprises, (a) an eluent generator, which comprises, (i) a housing configured to be pressurizable by gas. The housing includes an annular void defined by the housing. The housing includes a gas inlet for the gas and a gas outlet for the gas in fluid communication with the annular void. The eluent generator also includes (ii) a membrane permeable to the gas. The membrane defines an eluent flow channel disposed within the annular void. The eluent flow channel has an eluent precursor fluid inlet and an eluent outlet. The eluent generator further includes (b) a source of gas in fluidic communication with the gas inlet; and (iii) a source of the eluent precursor fluid. Downstream of the eluent generator and in fluidic communication with the eluent outlet is a sample interjector and a chromatography column configured to perform the chromatographic separation of the analyte. Exemplary embodiments include a valve, a vacuum, a trap, or a reservoir of inert gas (e.g., $N_2$) at the gas outlet.

Exemplary systems of the invention further include a member selected from a gas input solenoid in fluidic communication with said source of gas and the gas inlet and interposed therebetween, a gas exhaust solenoid in fluidic communication with the gas outlet, and a combination thereof. According to these embodiments, the eluent generator can be pressurized with the gas to a pre-selected pressure, providing the operator the ability to control the amount of gas traversing the gas permeable membrane and entering the eluent flow channel, thereby controlling the concentration of gas (or reaction products between the gas and the eluent precursor) in the eluent flow channel.

The system and its components, e.g., the eluent generator, can be controlled manually or electronically. In an exemplary embodiment, at least a component or substructure of the system is controlled by a microprocessor or similar device. For example, to control the pressure of the gas in the eluent generator, the gas input solenoid, the gas exhaust solenoid and a combination thereof is controlled by a controller such that pressure of the gas within said eluent generator is controlled to a pre-selected pressure by the controller. Thus, in one embodiment, the gas input solenoid is open and the gas exhaust solenoid is closed, allowing the eluent generator to be pressurized with the gas. In various embodiments, the gas exhaust solenoid is open and the gas input solenoid is closed, allowing the device to be depressurized. In yet another embodiment, the gas input solenoid is open and the gas exhaust solenoid is open, allowing the device to operate at essentially atmospheric pressure with respect to the gas.

In a still further embodiment, the gas exhaust is fluidically connected to a vacuum, which promotes the passage of the gas across the external surface of the gas permeable membrane. In an exemplary embodiment, the vacuum allows the gas to be present in the eluent generator at a pressure that is less than atmospheric pressure. Thus, the device provides multiple configurations for adjusting the pressure of the gas and, therefore, the concentration of the gas or reaction components derived from the gas, in the eluent.

In various embodiments, the system further comprises a pump in fluidic communication with the eluent flow channel inlet. The pump is configured to supply the eluent precursor fluid to the eluent flow channel. The Engasser can be on the high pressure side or on the low pressure side of the pump depending on whether it is desirable for a particular application to drive the eluent precursor and eluent through the eluent flow channel or to pull the fluids through the flow channel.

The system is configured for the use of any gas permeable membrane in any format of eluent flow channel. In an exemplary embodiment, the gas permeable membrane is configured to permit passage of the gas from the annular void into the eluent flow channel and prevent or retard passage of the eluent from the eluent flow channel into the annular void. An exemplary gas permeable membrane is Teflon AF®.

The system can be used with acidic gases, basic gases and gases which are neutral but which form acids or bases upon contacting the eluent precursor or the eluent. Exemplary gases include $CO_2$, a gas derived from a volatile acid, a gas derived from a volatile base, and ammonia. In some embodiments, it is desirable to use two or more gases. In some embodiments, the gases have different characteristics. Thus, in various embodiments, the system is configured to run in a gradient mode in which two or more eluents containing different gases or products derived from gases are mixed.

The system of the invention is versatile and is of use in the formation of organic eluents, aqueous eluents and combinations thereof in both isocratic and gradient formats. In an exemplary embodiment, the eluent is an aqueous eluent and the eluent precursor fluid is an aqueous eluent precursor fluid.

An exemplary device of the invention is shown in FIG. 1. Eluent precursor fluid enters the eluent flow channel 4 contained in housing 3 through eluent precursor fluid inlet 1. The exemplary device includes a coupling union 2 that includes three fluid ports. Coupling union 2 fluidically couples eluent precursor inlet 1 to eluent flow channel 4 and a downstream coupling union fluidically couples eluent precursor outlet 7 to eluent flow channel 4. Coupling union 2 also fluidically couples gas inlet 5 to the annular void within the housing 3 and the downstream coupling union fluidically couples gas outlet 6 to the annular void within the housing 3. The gas enters the annular void within the housing 3 through gas inlet 5, contacting the exterior surface of gas permeable membrane 8 of the eluent flow channel before existing the housing through gas outlet 6. Spacer inlet/outlet tubing 9 helps form a seal between coupling union 2 and gas permeable membrane tube 8. The resulting eluent exits the eluent flow channel through eluent outlet 7.

In various embodiments, the system of the invention further comprises a delay device in fluidic communication with the eluent outlet and the chromatography column and interposed therebetween. The delay device provides for a finite delay, of the order of several to 100 seconds, between the gas dissolving in the eluent at the generator and the resulting liquid reaching the chromatography column. This may be of particular relevance with $CO_2$ as the half life for its conversion to $H_2CO_3$ is ~20 s.

Figure 2:
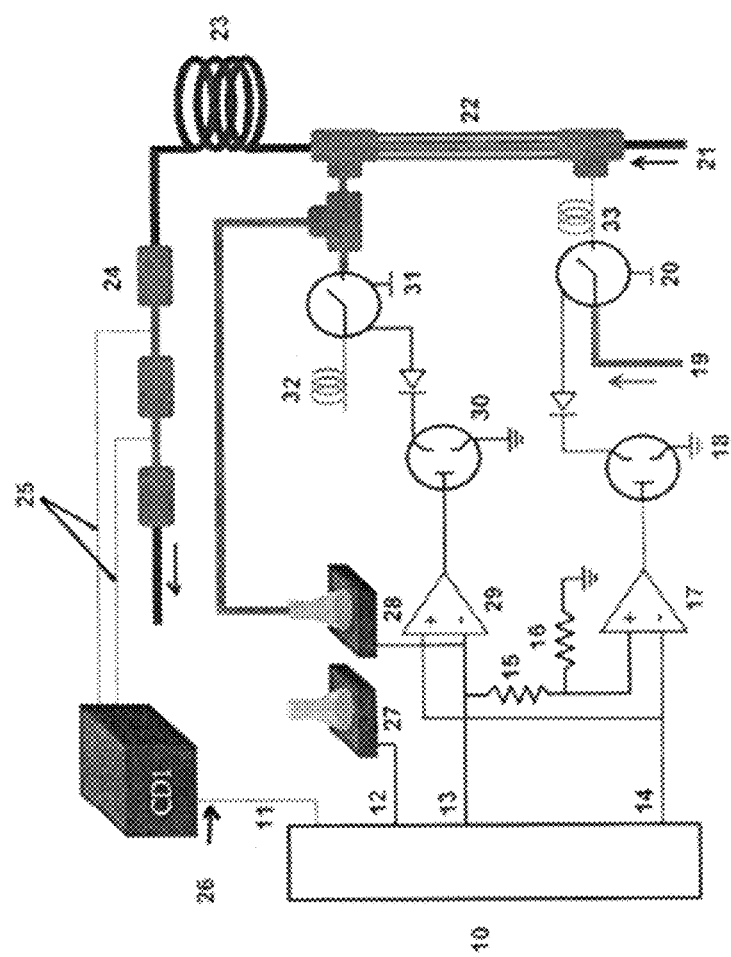
FIG. 2 is an exemplary eluent generator of the invention.

An exemplary embodiment of the invention is shown in FIG. 2. The system is controlled by microprocessor 10 (e.g., FreeSoC), which is operatively connected to comparators 17 and 29 through lines 14 (12 bit Aout) and 13 (12 bit Ain1), respectively. Comparator 29 is operatively linked to transistor 30, and comparator 17 is operatively linked to transistor 18. An exemplary transistor is a MOSFET. The microprocessor is also attached to pressure sensor 27 through line 12 (12 bit Ain2) and to conductivity detector CD1. Resistor 15 connects line 13 and comparator 17. Gas inlet solenoid 20 controls the flow of gas from gas inlet 19 into capillary 33 and then into eluent generator 22. Eluent precursor enters the eluent generator through eluent precursor inlet 21. Gas outlet solenoid 31 is operatively coupled to the gas outlet by means of a T-junction, which also connects the gas outlet to pressure sensor 28. Solenoid 31 is also coupled to capillary 32. In an embodiment, a vacuum pump (not shown) can be coupled to solenoid 31 or capillary 32 so that the pressure of the annular void of the housing of eluent generator 22 can be lowered to less than atmospheric pressure. The eluent outlet of eluent generator 22 is fluidically coupled to coil 23, which is of use to further dissolve the gas in the eluent or react the components of the gas with the eluent. Outlet from this coil is routed to high pressure conductivity cell 24 and exits from this cell to the chromatographic system, e.g., to the chromatography column and other downstream components. Conductivity detector CD-1 receives data from conductivity cell 24 via lines 25.

Figure 6:
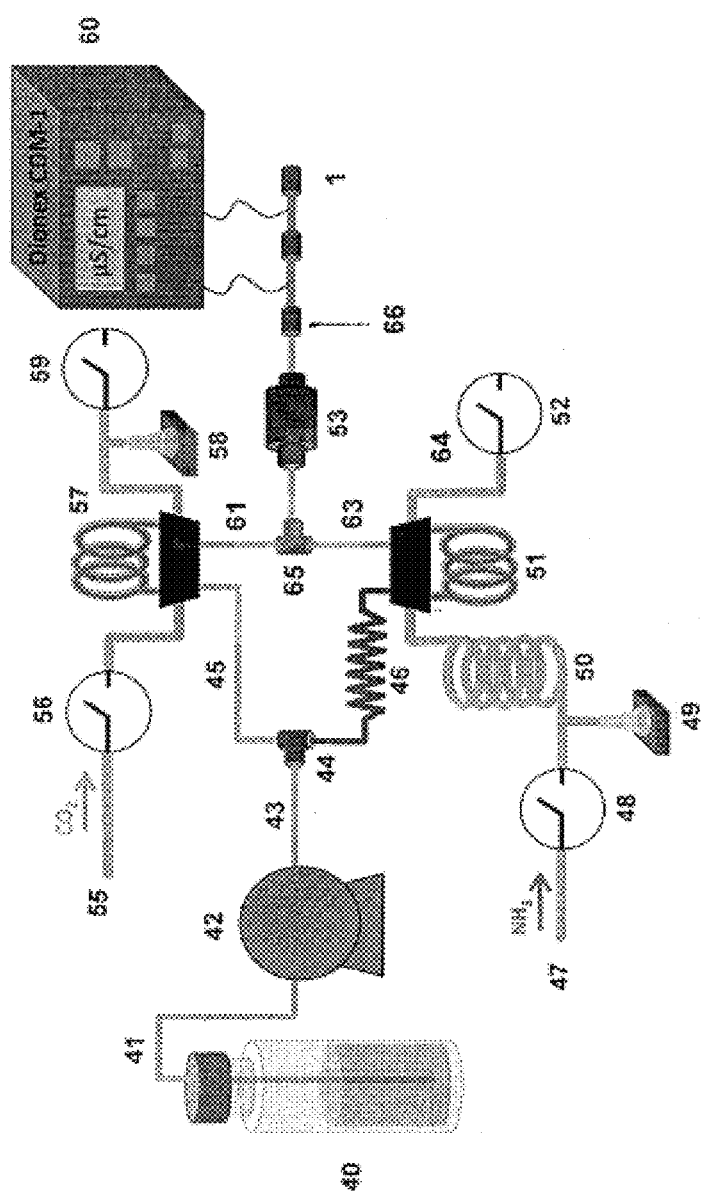
FIG. 6 shows the experimental setup for dynamic titration of $CO_2$ using $NH_3$ and for generating $NH_4^+/HCO_3^-/CO_3^{2-}$ buffers.

Another exemplary embodiment is shown in FIG. 6. Eluent precursor fluid is pulled from reservoir 40 through line 41 by pump 42, exiting the pump through line 43, which joins T-junction 44. In the upper branch, the eluent precursor flows through line 45 into Engasser 57, where it is contacted with $CO_2$, entering the Engasser through line 55. $CO_2$ flow into the eluent generator is controlled by solenoid 56. Excess $CO_2$ exits the Engasser through line 57, where the pressure is determined by pressure transducer 58. The flow of $CO_2$ out of the eluent generator is controlled by solenoid 59. In the lower branch, eluent precursor fluid enters line 46 and passes into Engasser 51. $NH_3$ enters the system through line 47, and is controlled by solenoid 48. $NH_3$ pressure is measured by pressure transducer 49. The $NH_3$ passes through buffer coil 50 and into the Engasser. Excess $NH_3$ exits the Engasser through line 64 and the flow through this line is controlled by solenoid 52. The eluent formed in the upper branch exits Engasser 57 through line 61. The eluent formed in the lower branch exits Engasser 51 through line 63. The eluents formed in the upper and lower branches are combined in T-junction 63 from which they are passed to gradient mixer 53. Conductivity of the eluent exiting the gradient mixer is optionally measured by means of high pressure conductivity cell 54. The signal from this cell is transmitted to conductivity detector 60. In an exemplary embodiment, the chromatography system includes one or more injection valves 66, chromatography columns or detectors after the gradient mixer 53 or high pressure conductivity cell 54.

In various embodiments, it is desirable to maintain the gas at a temperature higher than ambient temperature. For example, it may be desirable to prevent the gas from condensing from the gaseous state to the liquid state or to increase the pressure of the gas within the eluent generator. Gas permeation through a membrane is also temperature dependent, thus in various embodiments the device includes a thermostated enclosure to generate reproducible eluents containing the dissolved gas. Thus, in various embodiments, the system of the invention, e.g., the eluent generator, further comprises a heating device configured to heat at least a portion of the eluent generator, thereby maintaining the gas in a gaseous state with consistent membrane permeation.

When the heater is connected to the eluent generator or a portion thereof, it may be used to heat the entire eluent generator or a portion thereof. In an exemplary embodiment, the heater heats at least the gas input or a component thereof. In an exemplary embodiment, the heater heats the gas input and the gas input solenoid. The heater may be of any useful design, including resistance heaters, air heaters and jackets, liquid-based heaters and jackets, etc.

The system of the invention is of use in ion chromatography in both suppressed and non-suppressed modes. In an exemplary embodiment, the system further comprises a suppressor configured to suppress ions of said eluent, said suppressor disposed downstream of said chromatography column and in fluidic communication therewith.

In an exemplary embodiment, the system of the invention further comprises a suppressor downstream of and in fluidic communication with the chromatography column. Suppressed conductometric anion chromatography (SCAC) applications range from trace analysis in semiconductor manufacturing (Vanatta, L. E. *TrAC, Trends Anal. Chem.* 2001, 20, 336-345) to pharmaceutical analysis (Michalski, R. *Mini-Rev. Med. Chem.* 2014, 14, 862-872) to name a few. While SCAC excels in measuring strong acid anions, weak acid anions respond poorly or not at all. Even though acids with $pK_a < 7$ show some response, they do so in a nonlinear manner. Anions from very weak acids ($pK_a \geq 7.0$), e.g., silicate or cyanide are essentially not measurable.

Suppressed ion chromatography is a known technique for the analysis of ions. Suppression or stripping of the electrolyte is described in U.S. Pat. Nos. 3,897,213; 3,920,397; 3,925,019; and 3,926,559 by an ion exchange resin bed. A different form of suppressor column is described and published in U.S. Pat. No. 4,474,664, in which a charged ion exchange membrane in the form of a fiber or sheet is used in place of the resin bed. In this form of suppressor, the sample and eluent are passed on one side of the membrane with a flowing regenerant on the other side, the membrane partitioning the regenerant from the effluent of chromatographic separation. The membrane passes ions of the same charge as the exchangeable ions of the membrane to convert the electrolyte of the eluent to weakly ionized form, followed by detection of the ions. Other useful suppressors are disclosed in U.S. Pat. Nos. 4,751,004, 4,459,357, 4,403,039, 4,500,430 and 4,647,380, and 4,999,098.

In various embodiments, the system of the invention further comprises a detector configured to detect at least one component of the analyte. The detector is disposed downstream of said chromatography column and in fluidic communication therewith. A particular detection scheme is chosen based on the properties of the analytes. For example, in ion chromatography, analysis of nitrate, bromide or iodide can be pursued by ultraviolet detection (UV) since these analytes absorb in UV. However other common ions such as fluoride, sulfate, and phosphate do not absorb UV and so will not respond to direct UV detection. Those of ordinary skill in the art understand how to select the proper detector or detectors for a particular analysis.

Another exemplary system of the invention includes one or more evaporative type of detector. In this technique, the eluent along with the analyte are outputted (e.g., nebulized) from the chromatography column and then evaporated where the analyte remains as a residual solid. The residual solid particles can then be detected with an evaporative light scattering detector, a charged aerosol detectors, and/or an electrospray ionization mass spectrometer. The charged aerosol detector (CAD) nebulizes the effluent flow and creates charged particles that can be measured as a current proportional to the analyte concentration. Details regarding the charged aerosol detector can be found in U.S. Pat. Nos. 6,544,484; and 6,568,245, which are hereby fully incorporated by reference herein. Evaporative light scattering detector (ELSD) includes a nebulizer receiving a solution eluting from a separation column, then atomizing and spraying the solution as droplets, which dry to form residue aerosol particles. An air stream carries the residue particles past a beam of light, each particle scattering (reflecting or refracting) the light as it intersects the beam. One or more photodetectors sense the scattered light. The scattered light intensity increases with the size of the particle. Accordingly, the amplitude of the photodetector output signal is used to measure particle size. Details regarding an example of an ELSD can be found in International PCT Publication WO 2010/068272, which is hereby fully incorporated by reference herein. In various embodiments, the evaporative step removes the volatile and ionically charged eluent that can interfere with mass spectrometry.

In various embodiments, the system includes one or more conductivity detectors. Conductivity detection is a bulk property detection and the total conductance depends on the nature of the ions via the charge on the ion and the mobility and the concentration in a sample. The specific conductance of a solution is the sum of the concentration-mobility product of the different ions present. It is well known that equal concentrations of specific different compounds, e.g. NaCl and HCl, have vastly different specific conductance.

According to the present invention, an exemplary volatile amine is an amine capable of permeating through the permeable membrane of the permeant membrane device of the invention from a solution of the volatile amine in which the membrane is in contact while an eluent stream containing one or more weakly ionizable acid flows within the annulus of the permeable membrane. Exemplary volatile amines of use in the present invention include those having a general structure according to Formula I:

in which $R^1$, $R^2$ and $R^3$ are selected from H and substituted or unsubstituted alkyl. Exemplary alkyl moieties include $C_1$, $C_2$, $C_3$, $C_4$, $C_5$, $C_6$, $C_7$, and $C_8$ straight, branched chain and cyclic substituted or unsubstituted alkyl moieties. In various embodiments, two or more of $R^1$, $R^2$ and $R^3$, together with the nitrogen to which they are joined to form a ring structure. The amines can be used individually or in combination.

Exemplary volatile amines include, without limitation, (methyl)$_n$amine, (ethyl)$_n$, (propyl)$_n$amine, and (butyl)$_n$amine, in which n is 1, 2, or 3; alkanolamines (including, but not necessarily limited to, monoethanolamine (MEA), methyldiethanolamine (MDEA), diethanolamine (DEA)); ethylenediamine (EDA), methoxypropylamine (MOPA), diethylaminoethanol (DEAE) and the like and mixtures thereof. Although ammonia is not strictly speaking an amine, in the context herein ammonia is included in the same group of nitrogen compounds as amines.

In various embodiments, the useful amines include relative stronger amines having a pKa between about 10.5 to about 12. In one non-limiting embodiment, the amine does not contain oxygen. In another non-restrictive embodiment, the amines are di-alkylamines which have a pKa range of between about 10.7 to about 11.4. In various embodiments, the amine has a normal boiling point less than about 95° C., e.g., less than about 70° C., less than about 50° C., or less than about 40° C. Suitable amines include, but are not limited to, dimethylamine, diethylamine, dipropylamine, di-isopropylamine, di-n-butylamine, diisobutylamine, di-sec-butylamine, di-tert-butylamine, pyrrolidine, piperidine, and combinations (e.g., mixtures) thereof.

Exemplary volatile amines of use in the invention have sufficiently low conductance at the concentration used such that they do not excessively interfere with detection of the analytes.

According to the present invention, an exemplary volatile acid is an acid capable of generating a gas, which can permeate through the permeable membrane of the eluent flow channel of the eluent generator of the invention from a solution of the neat or diluted volatile acid while an eluent precursor/eluent stream flows within the lumen of the permeable membrane. Useful volatile acids include those acids which have a pKa range from <0 to about 4. Another definition of volatile acid is on that is relatively readily removed from a solution under vacuum. Exemplary volatile acids include all haloacids (e.g., HF, HCl, HBr, and HI) as well as methanesulfonic acid, toluenesulfonic acid, carboxylic acids such as formic acid, etc., and other acids that at least 99% of which can be removed under vacuum (e.g., <10 mm Hg pressure) within 24 hours.

Any useful concentration of gas can be incorporated into the eluent flow channel within the permeable membrane of the eluent flow channel. In exemplary embodiments, the gas concentration in the eluent solution will vary for the specific chromatographic mode used. For the separation of weak acids by a $CO_2$ eluent, typically useful $CO_2$ concentrations range from 5 to 500 mM $CO_2$. In carbonate bicarbonate eluent preparation for suppressed ion chromatography, the useful range is from very low (<~1 mM) to 30 mM total carbonate carbon. In $NH_3$—$CO_2$ gradient applications, one or the other eluent component will typically start at zero concentration and range up to 250 and 500 mM, respectively, for $NH_3$ and $CO_2$.

In an exemplary embodiment, the invention uses a high concentration of gas, e.g., $CO_2$, $NH_3$ or a gas derived from a volatile base or volatile acid external to the membrane, and the gas is at least moderately permeable through the membrane. In this manner, the desired concentration of the gas within the eluent flow channel is reached. A high external concentration of gas coupled with a modest permeability of these components across the membrane ensures that, in exemplary embodiments, the external gas needs be only infrequently replenished. By "high external concentration" it is intended that the concentration of the gas be sufficiently high so as to not require constant changing, replacement or replenishment.

In an exemplary embodiment, the device of the invention includes a pressure readout and gas is added to or removed from the eluent generator automatically based upon the measured gas pressure and desired concentration of the gas or its derived species in the eluent.

An exemplary gas source is a compressed gas cylinder, e.g., for $NH_3$ and $CO_2$.

In various embodiments, a small external gas volume is desirable since it results in less wasted gas, particularly when a gradient is run.

Though recited in terms of certain ranges, it will be understood that all ranges from the lowest of the lower limits to the highest of the upper limits are included, including all intermediate ranges or specific values, within this full range or any specifically recited range. It is within the ability of one of ordinary skill to select membrane permeability (e.g., molecular weight cutoff, length, composition, thickness, etc.) and the concentration and identity of the gas to achieve a desired concentration of base or acid within the eluent flow channel. In an exemplary embodiment, the device is capable of prolonged use without replacement or replenishment of the gas source or eluent precursor source.

The present invention also provides methods of using the systems and devices disclosed herein. In an exemplary embodiment, the invention provides a method of performing a chromatographic separation using a system of the invention. The system comprises: (a) an eluent generator, comprising: (i) a housing configured to be pressurizable by gas, comprising an annular void defined by the housing, a gas inlet for the gas and a gas outlet for the gas in fluid communication with the annular void. The eluent generator also comprises: (ii) a membrane permeable to the gas defining an eluent flow channel disposed within the annular void and having an eluent precursor fluid inlet and an eluent outlet; (ii) a source of gas in fluidic communication with said gas inlet; (iii) a source of the eluent precursor fluid; and (b) a chromatography column disposed downstream of and in fluidic communication with the eluent outlet. An exemplary method comprises: (a1) flowing the eluent precursor fluid through the eluent flow channel while the annular void is maintained under positive pressure of the gas. The positive pressure is selected to be of a magnitude sufficient to cause the gas to cross the gas permeable membrane, dissolving it in said eluent precursor fluid, thereby forming said eluent. Step (b1) includes, passing the eluent from the eluent outlet into the chromatography column. Step (c1) includes contacting the chromatography column with the analyte, thereby performing the chromatographic separation of the analyte.

As will be apparent to those of skill in the art, an analyte is injected onto the chromatography column, and at least one component of the analyte is eluted from the chromatography column by eluent generated by the eluent generator flowing through the chromatography column. In various embodiments, the at least one component of the analyte is detected by a detector following its elution from the chromatography column.

The eluent precursor can be any useful liquid including, without limitation, e.g., water, aqueous bases, e.g., NaOH (aq), $NH_4OH$(aq), aqueous acids, e.g., HCl(aq), $H_2SO_4$ (aq), organic solvents, e.g., polar organic solvents, e.g., acetonitrile, methanol, ethanol, etc. and mixtures of water and aqueous acids, bases and/or salts with organic solvents. In various embodiments, acids, bases, and salts do not exceed about 200 mM in the eluent precursor. In various embodiments, appropriate selection of membrane geometries/type and gas pressure is deliberately chosen to generate gas-derived eluent component concentrations as high as 1 M.

In various embodiments, the eluent precursor is selected from aqueous NaOH or KOH. In an exemplary embodiment, NaOH or KOH can be present in the eluent precursor at a concentration of from about 0.001M to about 200 mM.

In various embodiments, the gas is a member selected from $CO_2$, ammonia, a gas derived from a volatile amine and a gas derived from a volatile acid.

The system of the invention is highly versatile and, because a wide range of eluents of different formats can be generated, the invention provides methods in which the eluent format is an isocratic format or a gradient format.

Because of this versatility, a wide range of different chromatographic procedures can be practiced using the system of the invention. Thus, the invention provides methods of chromatographic separation as varied as ion exclusion, ion exchange, chiral amine separation, amino acid separation, and protein separation, including separation of monoclonal antibodies.

One of the sources of the versatility of the system and the methods of use in conjunction with the system is the ability to predictably and reproducibly control the content and composition of the eluent produced with the eluent generator of the instant invention. Thus, in various embodiments, the invention provides a method in which, prior to performing a separation, the system is controlled to produce an eluent having a pre-determined composition. In an exemplary embodiment, the controlling comprises, (a) selecting the gas, and pre-determining; (i) pressure of the gas in the annular void; (ii) composition of the eluent precursor solution in the eluent flow channel; and (iii) flow rate of the eluent precursor solution through the eluent flow channel. The controlling further comprises, (b) controlling the eluent generator such that; (i) the pressure of said gas in the annular void is maintained at the pre-determined pressure; (ii) the composition of the eluent precursor fluid is maintained at the predetermined composition; and (iii) the flow rate of the eluent precursor fluid in the eluent flow channel is maintained at the predetermined flow rate, thereby producing said eluent having said pre-determined composition.

The system of the invention includes eluent generators in which a gas is dissolved in the eluent precursor/eluent. Also provided are systems in which the gas reacts with the eluent precursor/eluent in the eluent flow channel, forming new species for use as components of the eluent. Thus, it is desirable in certain embodiments to predetermine the rate of dissolution of the gas in the eluent precursor/eluent and/or the rate of reaction of the gas with the eluent precursor/eluent in the eluent flow channel. The pre-determined values of gas solubility and/or dissolution rate and/or gas reaction with the eluent precursor/eluent allow determining a concentration of the gas and/or a reaction product between the gas and the eluent precursor/eluent in the eluent precursor/eluent in the flow channel. In various embodiments, the rate of reaction of the gas with the eluent precursor is determined, thereby determining concentration of a reaction product resulting therefrom in the eluent.

As noted above, the system of the invention provides eluents in both isocratic and gradient formats. When a gradient format is desired, a parameter selected from: (i) the pressure of the gas in the annular void; (ii) the composition of the eluent precursor fluid; (iii) the flow rate of the eluent precursor fluid in the eluent flow channel; and (iv) a combination thereof is maintained for a pre-determined time after which it is varied, thereby producing the eluent in a gradient format. As those of skill in the art are aware, the gradient may include two or more eluent components, which vary in concentration, pH, composition, etc. The gradient can be selected to have any convenient profile and duration.

A key component of the systems and methods set forth above is the eluent generator of the invention. In an exemplary embodiment, the eluent generator is configured for generating an eluent of a pre-determined composition and for incorporation into a system for chromatographic separation of an analyte. An exemplary eluent generator includes: (a) a housing configured to be pressurizable by gas. An exemplary housing includes an annular void defined by the housing, a gas inlet for the gas and a gas outlet for the gas. Both the gas inlet and gas outlet are in fluid communication with the annular void within the housing. The eluent generator also includes, (b) a membrane permeable to the gas. The membrane defines an eluent flow channel disposed within the annular void. The eluent flow channel has an eluent precursor fluid inlet and an eluent outlet. The outlet is configured for coupling to a chromatography column and fluidically communicating therewith. To control the gas flow and pressure within the eluent generator, a first solenoid is coupled to and communicates fluidically with the gas inlet. The solenoid is optionally controlled by a first controller. Similarly, the eluent generator includes a gas inlet coupled to and communicating fluidically with a second solenoid. The second solenoid is optionally controlled by a second controller. The first and second controller can be the same controller. In an exemplary eluent generator and system of the invention, the first controller and the second controller are programmed to operate cooperatively to control pressure of the gas in the annular void at a predetermined value, thereby generating the eluent of said pre-determined composition.

The foregoing descriptions of specific embodiments of the present invention have been presented for purposes of illustration and description. They are not intended to be exhaustive or to limit the invention to the precise forms disclosed, and obviously many modifications and variations are possible in light of the above teaching. The embodiments were chosen and described in order to best explain the principles of the invention and its practical application, to thereby enable others skilled in the art to best utilize the invention and various embodiments with various modifications as are suited to the particular use contemplated. It is intended that the scope of the invention be defined by the Claims appended hereto and their equivalents. All references are incorporated herein by reference in their entirety.

EXAMPLES

Example 1

Eluent Generator Design and Control

The construction of the Engasser is shown in FIG. 1. While the permeative introduction $NH_3$ and $CO_2$ are largely discussed here, it should be readily understood that any permeable fluid can be introduced in this fashion. What is formed in the liquid in the lumen will depend on the composition of the influent liquid. With $CO_2$ as the Engasser gas, a solution of pure carbonic acid will be the effluent with pure water as the influent, with a base solution as the influent, a variable composition that can vary all the way from carbonic acid to bicarbonate to carbonate can be generated.

An illustrative example for an engasser device was presently constructed by first inserting the end of a piece of Teflon AF® tubing (0.28 mm i.d.×0.68 mm o.d.) into a 1/16" o.d. tubing (0.762 mm i.d.) that is not particularly permeable to $CO_2$. Teflon AF is tradename for an amorphous fluoropolymers based on copolymers of 2,2-bistrifluromethyl-4,5-difluro-1,3-dioxole. This tube is then swaged down upon the Teflon AF® using standard polyetheretherketone (PEEK) chromatography fittings (e.g., a coupling union). The Teflon AF® then is fed through a PEEK tee (1.27 mm thru hole), 1/8" o.d., 1/16" i.d. PTFE Teflon® or PEEK tubing, (very low $CO_2$ permeability), another PEEK tee, and finally into another length of $CO_2$ impermeable tube which again is swaged down on the Teflon AF®. This connecting impermeable tubing is then connected to the rest of the chromatography system. The length used depends on the eluent flow rate and concentration desired.

Application of the gas pressure to the device may be accomplished most simply using a pressure regulator, but this results in only a static pressure that is not programmable by the user. Experiments carried out in this report used a solenoid valve setup that allowed analog control of the pressure (FIG. 2). Digital pressure controllers are available for inert gases and may be more convenient to use if compatible with the gas to be introduced (Mini Pressure Controller).

The solenoid setup was controlled using a FreeSoC board which contains a Cypress Semiconductor P5 programmable system on a Chip. The device was configured to allow for data acquisition of the pressure sensors and a high pressure conductivity cell as well as analog outputs to control the pressure. The pressure was controlled using 2 LM311 comparators and, 2 MOSFETS, and 2 solenoid valves (SV). The analog out from the FreeSoC is directly coupled to both comparators but on opposite inputs. The high pressure sensor output (this sensor only provides gauge pressure and not absolute) is wired to the other terminals of the comparator and is also recorded using the FreeSoC. It was necessary to step the voltage down to the input of the comparator that controls the source valve to prevent continuous venting and filling. When a particular comparator has a high output, (the +input terminal is less than the −input terminal), the MOSFET energizes the solenoid valve SV connected to it. Silica capillaries (150 μm i.d., ~20 cm length) are used to reduce the gas introduction rate into the jacket to prevent immediate over pressurization of the device that will result in immediate venting. Similarly, silica outlet capillaries are used to limit the venting rate. An ambient pressure sensor is used to correct for any changes in atmospheric pressure. This is generally not an issue at a given location but can be important in translating elution/eluent conditions exactly if a method from a reference laboratory is to be accurately implemented in another varying considerably in altitude (and hence ambient pressure).

Permeation is governed by the partial pressure of the gas across the membrane. This means that at zero gauge pressure there is still ~1 atm partial pressure of the gas to be introduced in the jacket and thus there will still be permeation through the membrane. The dynamic range can be improved by adding a vacuum system, such as that commonly used with current degassers used in electrodialytic eluent generation or by a He/$N_2$ flush system, as these gases are already often available for pressurizing eluent reservoirs. A hydration or delay coil is shown after the Engasser. This is relatively unique to $CO_2$ introduction and is needed because the hydration of $CO_2$ ($CO_2+H_2O \rightarrow H_2CO_3$), especially into pure water or media of low [OH⁻] is relatively slow (the dehydration step is fast in comparison) (Soil and Byrne, Mar.Chem. 2002, 78 (2) 65-73). A hydration coil or catalyst is therefore particularly beneficial when a pure carbonic acid eluent is desired as used in Ion Exclusion Chromatography. The conductivity of the solution was measured after the coil for evaluating the $CO_2$ introduction rate. Note that the conductivity was always higher after the hydration coil because of slow hydration kinetics. The conductivity measurement cell was simply two stainless steel HPLC tubes used as electrodes connected and electrically separated by a PEEK union. The conductivity was measured by a Dionex CDM-1 detector, the analog output of which was acquired by the FreeSoC.

An embodiment of the eluent generator can use two gases, e.g., $NH_3$ and $CO_2$. Both of these gases liquefy at modest pressures (relative to HPLC) and ambient temperature. At 25° C., for example, $CO_2$ liquefies at ~930 psi while $NH_3$ becomes a liquid at ~145 psi. As ambient pressure is ~14 psi, this only allows an order of magnitude of control for $NH_3$ pressure compared to almost 2 orders of magnitude for $CO_2$ if vacuum or inert gas flush is not used at the low end. Especially with $NH_3$, it was also found necessary to keep the gas introduction valve heated; decompression of $NH_3$, commonly used as a refrigerant gas, through the valve causes the temperature to drop and leads to $NH_3$ condensation. Additional complications caused by this behavior include liquid $NH_3$ flowing through the valve and accumulating in the Engasser; even after the inlet valve is closed, the pressure continues to increase as the liquid warms up and evaporates. $NH_3$ is not vented directly into the laboratory air but through an acid trap; while a bubbler containing a dilute sulfuric acid solution can be used, a cartridge packed with acid impregnated silica gel or ammonium or sodium bisulfate (into which an exhaustion indicator like bromthymol blue can be incorporated is convenient. A solid trap prevents problems associated with potential back aspiration of a solution phase acid into the Engasser.

Note also that while $CO_2$ has to be introduced in a high pressure format because of its much lower solubility, $NH_3$ has a very high Henry's law constant (highly soluble in water), 28% w/w or 14.5 mol/L $NH_3$ has a vapor pressure of only 1 atm. Ammonia can thus also be introduced through a low pressure Engasser before the pump if desired. Even with introduction on the high pressure side, pressures in excess of 100 psi $NH_3$ were not needed when the proper length of tubing was chosen.

Example 2

Permeation Rate

Figure 3:
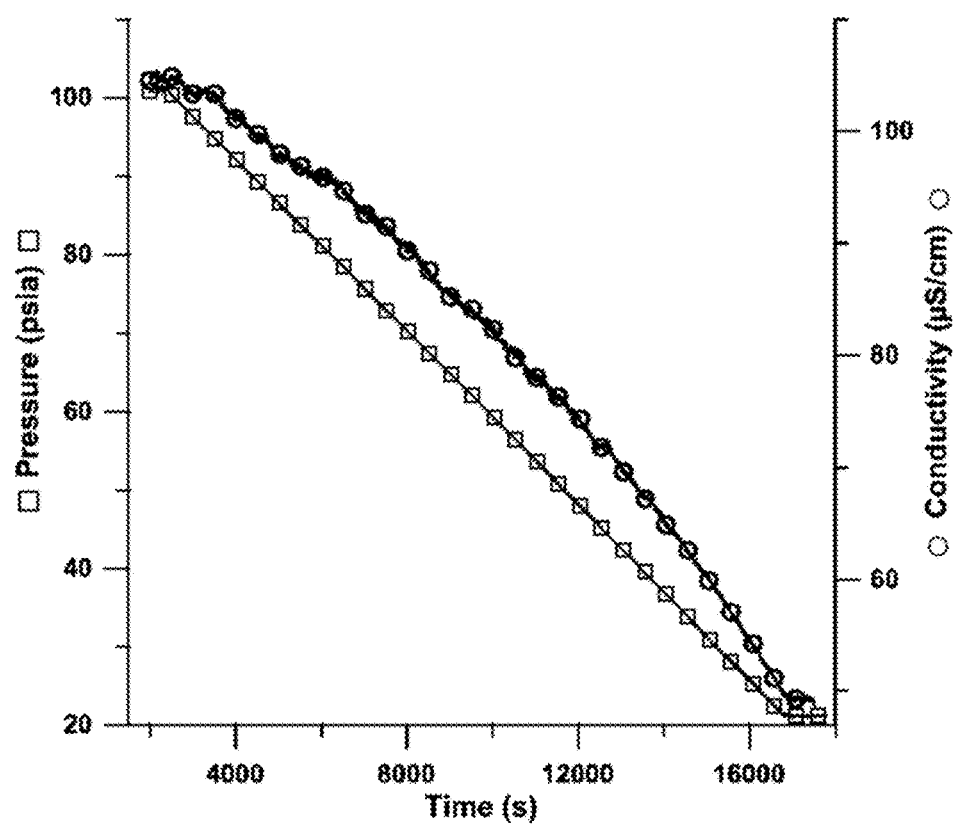
FIG. 3 is a graph showing the pressure and resultant solution conductivity over time for $CO_2$ permeating through a 160 cm long membrane.
Figure 4:
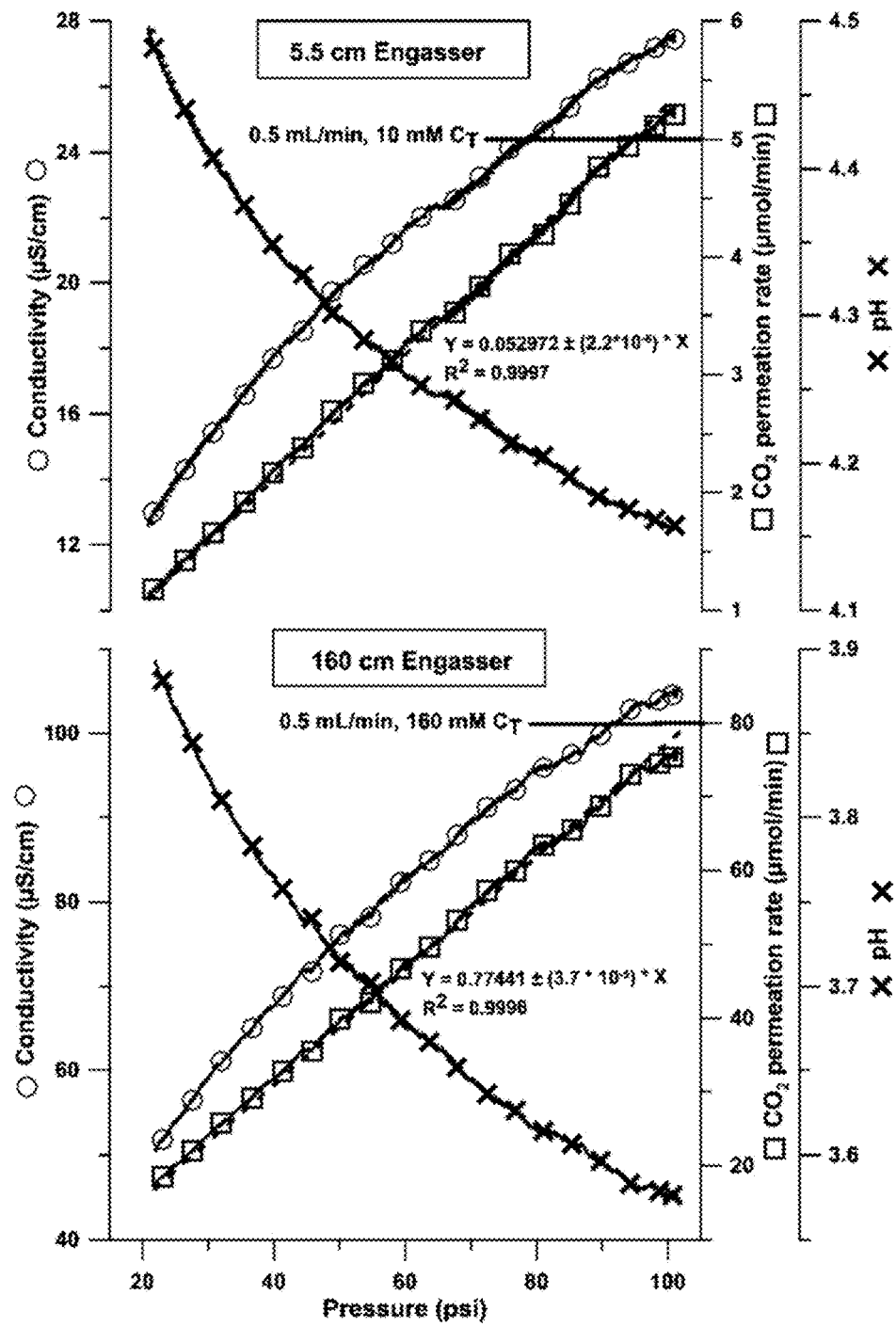
FIG. 4 is a graph showing solution conductivity, pH, and $CO_2$ permeation rate as a function of pressure through 2 different membrane lengths.

The rate of permeation of $CO_2$ or $NH_3$ into pure water was measured using conductivity as shown in FIG. 2. A back-pressure coil was used to generate 1000 psi at 0.5 mL/min. The applied $CO_2$ or $NH_3$ pressure was changed gradually over time and the conductivity and the applied pressure values were recorded. FIG. 3 shows illustrative data for $CO_2$ permeating through a 160 cm long Engasser. Based on the known limiting equivalent conductance of $HCO_3^-$ and $H^+$, the conductivity data can be used to calculate their concentrations and hence pH. The known dissociation constants relevant for the system then permit the estimation of the total amount of permeated $CO_2$ as well as a permeation rate per unit pressure of $CO_2$. FIG. 4 shows the relationship between pressure, conductivity, pH, and permeation rate for $CO_2$ using 2 Engasser lengths differing by a factor of 30). Because $H_2CO_3$ is a weak acid, the conductance is nonlinear with pressure. The total dissolved concentration is linear however with pressure ($R^2 \geq 0.9996$). We found that the 5.5 cm Engasser had a permeation rate per unit length (9.7 nmol/cm/min/psi) almost twice that of the 160 cm Engasser (compared to 4.9 nmol/cm/min/psi). The present systems are non-equilibrium systems—the solution composition in the lumen will never reach equilibrium with the external gas pressure. The introduction rate does not increase linearly with increasing length because the internal $CO_2$ concentration/pressure increases along the length of the Engasser, resulting in greater differential pressure across the membrane in the entrance region that continually decreases with the downstream length. Using the Henry's law constant, the solution partial pressure can be calculated. For the 5.5 cm engasser, at a water flow rate of 0.5 mL/min, the solution partial pressure of $CO_2$ reaches 4.6% of the external $pCO_2$, while under the same conditions the 160 cm engasser reaches 68% of the equilibrium $pCO_2$. Obviously the overall rate of permeation will also be lumen flow dependent, reducing the flow will increase the degree to which equilibrium is approached by increasing the residence time in the Engasser, the effective permeation rate per unit time will decrease.

Figure 5:
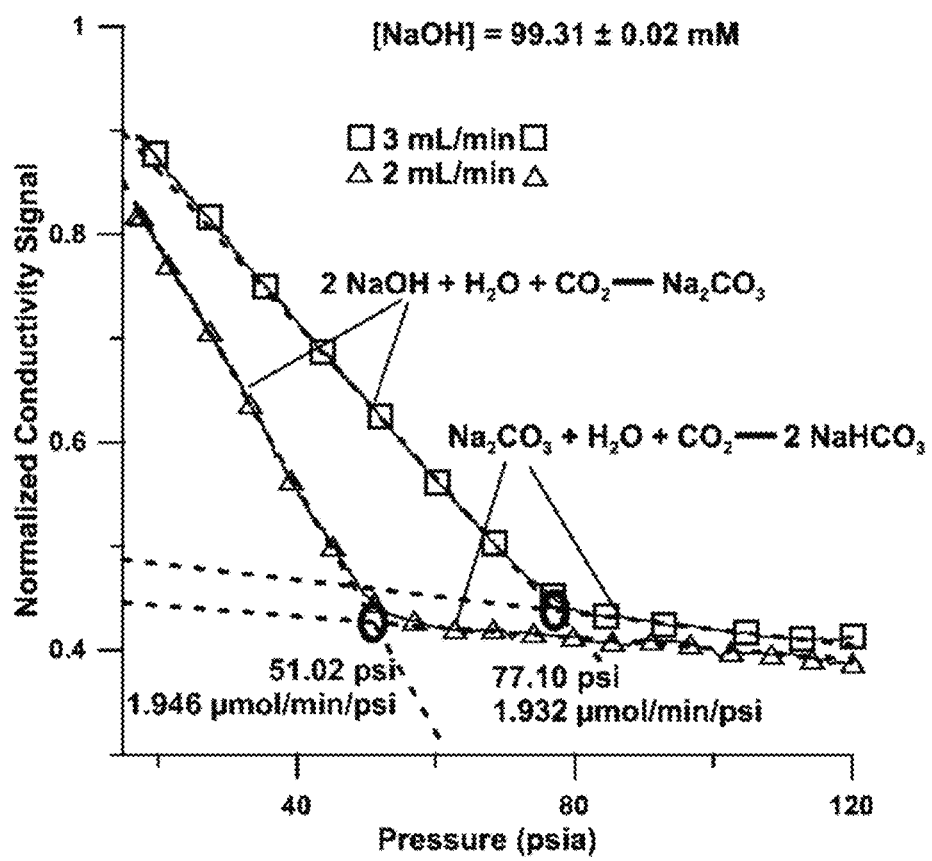
FIG. 5 is a graph showing solution conductivity vs. pressure of $CO_2$ introduced into a solution containing NaOH through a 160 cm long Engasser. Conductivity was normalized to a solution of only NaOH.

In a situation where the introduced gas reacts immediately with the lumen fluid (i.e., eluent precursor/eluent), for example when $CO_2$ is introduced into a NaOH solution in the lumen, the gas partial pressure in the lumen effectively remains near zero until the reactive consumption stops. In this case the permeation rate remains independent of flow rate. Consider an online titration of NaOH flowing into the lumen with $CO_2$ (FIG. 5) using the 160 cm Engasser and varying the external $CO_2$ pressure while holding the influent NaOH concentration and flow rate constant. The $CO_2$ first reacts with the NaOH to form $Na_2CO_3$. Additional $CO_2$ is then consumed reactively to form $NaHCO_3$. Tangent based determination of the first equivalence point was determined at two different NaOH flow rates from which the permeation rate of the $CO_2$ could be calculated. Given the known input flux of NaOH, the permeation rate at the two different flow rates were calculated to be within 0.5% of each other, 1.94±0.01 µmol/min/psi. For this particular tubing this would be the maximum attainable permeation rate. Note that this value is 1.26× that of what the 5.5 cm Engasser exhibits with a water influent. Given that in this very short device the approach to equilibrium is <5% complete, the difference should have been less—suggesting that concentration polarization occurs within the lumen, meaning that the actual $pCO_2$ at the interior boundary layer of the wall is higher than in the bulk solution, thus reducing the permeation rate more than what will be estimated of the degree of attainment of equilibrium of the bulk solution. Predictably the average permeation rate for the much longer 160 cm engasser with a water influent was much lower (by 2.5× compared to the NaOH influent case).

Summary of permeation rate data for the various experimental devices are presented in Table 1. Note that the permeation rate/length is nearly constant for $NH_3$ regardless of flow rate or device length because of its much greater Henry's law solubility compared to $CO_2$ and the fact that $NH_4^+$ is a considerably stronger acid than $H_2CO_3$. From a practical standpoint, the greater extent of ionization also makes the slope of conductance vs. total dissolved amount steeper than in the case of $CO_2$, facilitating the measurement of the total permeated amount or the permeation rate (for which measurement at only one flow rate in this case is sufficient).

TABLE 1

Permeation Rate Constants for $CO_2$ and $NH_3$ of various lengths and eluent flow rates measured by titration or conductivity.

| Tubing Length (cm) | Titration (Y/N) | Flow Rate (mL/min) | Permeation Rate (umol/min/psi) | Permeation Rate/Length (nmol/min/psi/cm) |
|---|---|---|---|---|
| $CO_2$ | | | | |
| 160 | N | 0.5 | 0.774 | 4.840 |
| 5.5 | N | 0.5 | 0.053 | 9.631 |
| 160 | Y | 2 | 1.946 | 12.163 |
| 160 | Y | 3 | 1.946 | 12.163 |
| 40 | N | 0.2 | 0.169 | 4.228 |
| $NH_3$ | | | | |
| 160 | N | 0.5 | 1.300 | 8.125 |
| 5.5 | N | 0.5 | 0.055 | 9.949 |
| 160 | Y | 1 | 1.322 | 8.265 |
| 160 | Y | 1.25 | 1.377 | 8.604 |
| 40 | N | 0.2 | 0.345 | 8.630 |
| 40 | N | 0.2 | 0.382 | 9.562 |
| 40 | N | 0.2 | 0.355 | 8.879 |
| 25 | N | 0.2 | 0.231 | 9.231 |
| 25 | N | 0.2 | 0.233 | 9.311 |

Figure 7:
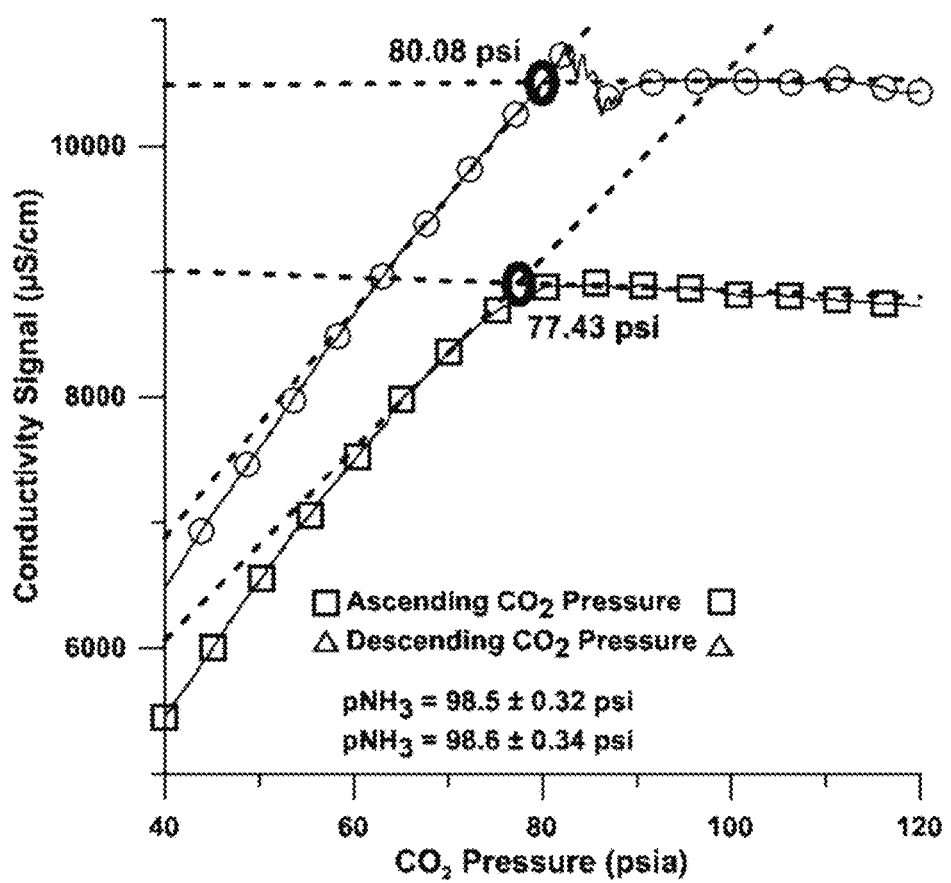
FIG. 7 shows titration of fixed $NH_3$ with $CO_2$. Note virtually identical $CO_2$ pressures at the end point from ascending and descending $pCO_2$ titration protocols. The minor difference arises due to hysteresis.

Once the $NH_3$ permeation rate for a system is known, a dynamic titration of $CO_2$ using $NH_3$ can be used to determine the $CO_2$ permeation rate under the given experimental conditions. The setup for performing this titration as well as generating an ammonium carbonate gradient is shown in FIG. 6. The bulk of the flow is sent through the $CO_2$ engasser since it is more sensitive to lower flow rates than $NH_3$. The $NH_3$ compatible valves readily available to us were relatively large resulting in significant system hysteresis. This was mitigated through the use of a long (2 m) buffer coil of PTFE tubing (3 mm od 1.5 mm id). FIG. 7 shows the results for titration of a fixed pressure of $NH_3$ with varying $CO_2$ pressures with both ascending and descending $pCO_2$. $CO_2$ reacts with $NH_3$ in $H_2O$ at first to form $(NH_4)_2CO_3$. The increase in conductivity that results from $CO_2$ introduction into ammonia is due both to the formation of $NH_4^+$ and $CO_3^{2-}$. Once $(NH_4)_2CO_3$ formation is complete there is only a minor decrease in conductance as the conversion of $CO_3^{2-}$ to less mobile $HCO_3^-$ is partly offset by the increase in $[NH_4^+]$ due to the decrease in pH. The net result is a virtual plateau in conductance. As the rate of ammonia introduction is known and will be equal to twice the $CO_2$ introduction rate on a mole basis at the $(NH_4)_2CO_3$ equivalence point. The ratio of the $CO_2$ to $NH_3$ pressures at the equivalence point can be multiplied by the $NH_3$ permeation rate to compute the $CO_2$ rate. Similarly a fixed $CO_2$ pressure can be titrated by varying the ammonia introduction rate; all of the resulting $CO_2$ permeation rate data are listed in Table 2 and are remarkably constant, no matter how it has been determined.

TABLE 1

Calculation of Permeation Rate of $CO_2$ by titration with $NH_3$. The fixed pressure is the constant pressure of the non-titrant gas.

| Titrant Gas | Fixed Pressure | Equivalence Pressure | $CO_2:NH_3$ Permeation Rate Ratio | $CO_2$ Permeation Rate (umol/min/psi) |
|---|---|---|---|---|
| $CO_2$ | 98.50 | 77.43 | 1.272116751 | 0.294837621 |
| $CO_2$ | 98.60 | 80.08 | 1.231268731 | 0.285370304 |
| $NH_3$ | 61.00 | 76.07 | 1.24704918 | 0.289027727 |
| Average | | | 1.250144887 | 0.289745217 |
| StDev | | | 0.020599217 | 0.020599217 |

Example 3

3.1 Ion Exclusion

In ion exclusion chromatography, the separation of weak acids is carried out based upon their diffusion into an occluded volume of a like charged resin and adsorption to the resin matrix. For efficient chromatography, typically a strong mineral acid is used to lower the pH of the separation environment and suppress weak acid ionization. However, this separation design results in poor sensitivity for suppressed conductometric detection compared to ion exchange chromatography because the eluent cannot be converted to water or to a weakly conducting acid like carbonic acid.

Figure 8:
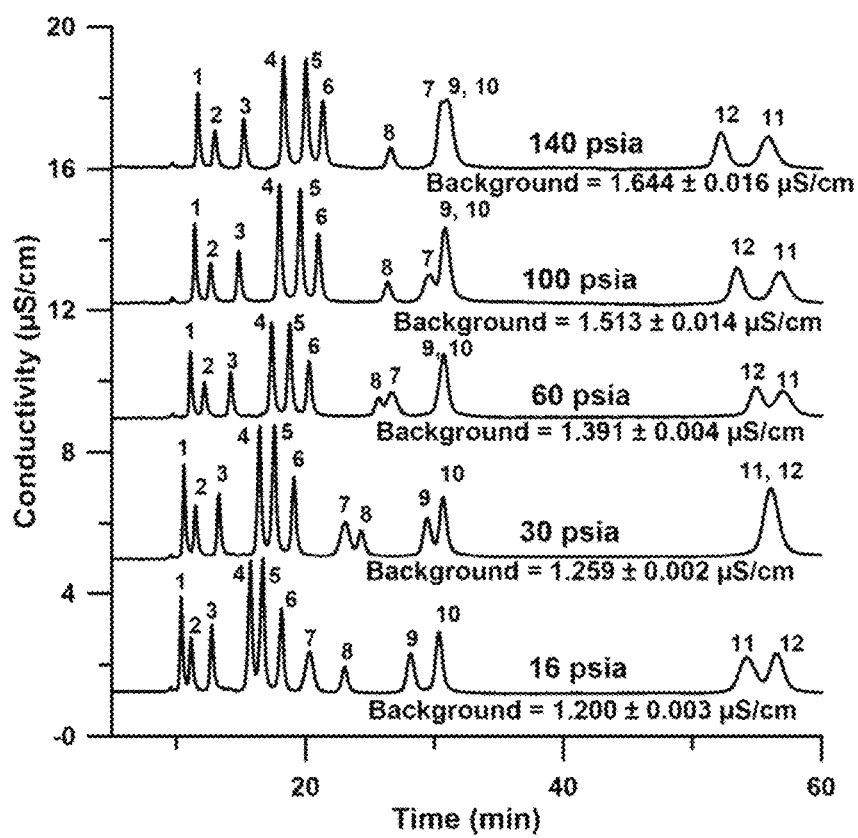
FIG. 8 shows isocratic elution of various organic acids on a Thermo Scientific™ Dionex™ IonPac™ ICE-AS6 column. The eluent contained up to 250 mM $CO_2$ 0.5 mL/min; Thermo Scientific™ Dionex™ IonPac™ ICE-AS6 column (9×250 mm); 160 cm Engasser; 16-140 psi (~25 mM-250 mM $CO_2$); 20 μL injection volume.
Figure 9:
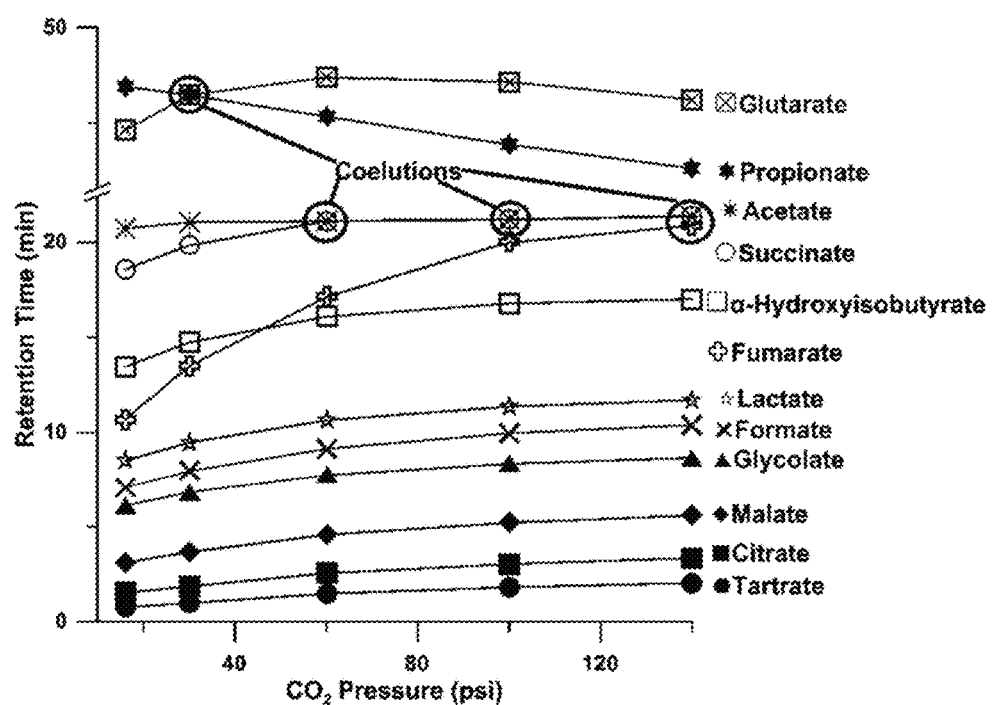
FIG. 9 is a graph showing peak retention time relationship with Engasser $CO_2$ pressure for the ion exclusion separations shown in FIG. 8.
Figure 10:
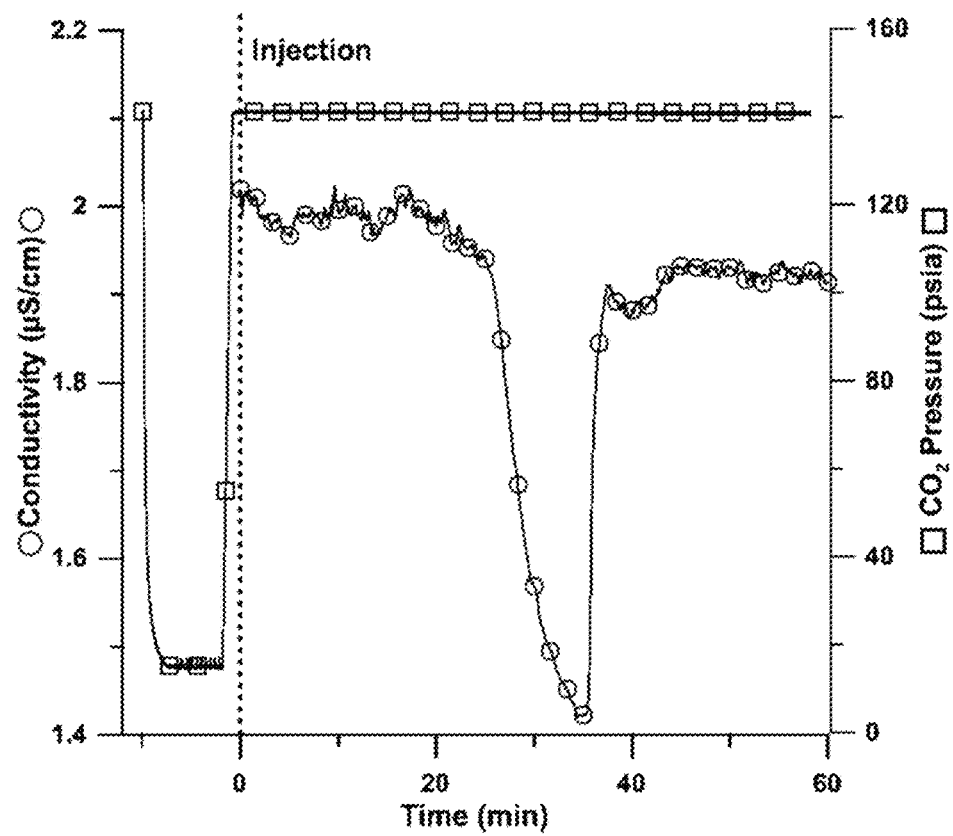
FIG. 10 is a graph showing gradient separation program and resultant background conductivity signal. The dip associated with the gradient can be seen nearly 40 minutes after being initiated.
Figure 11:
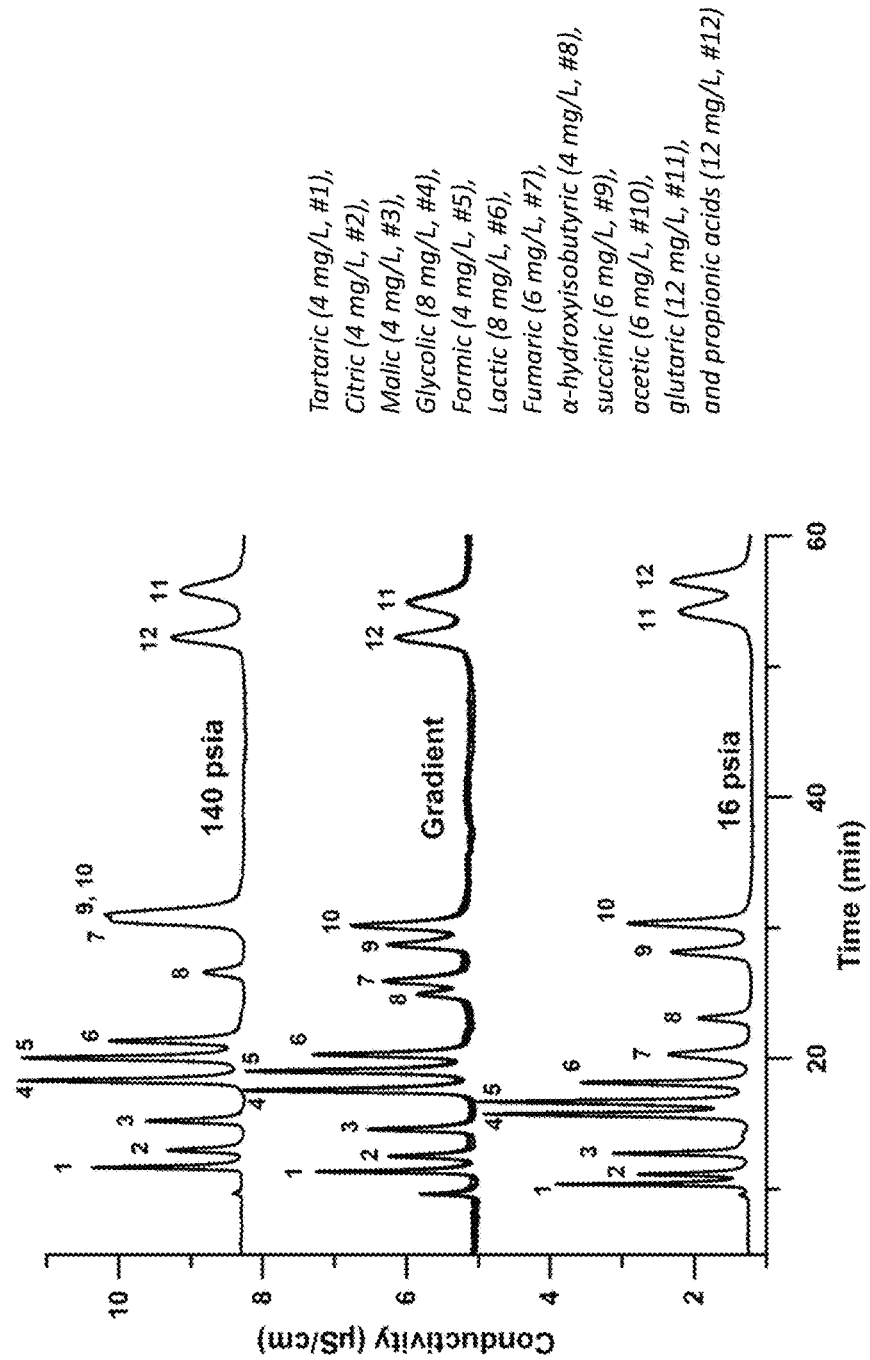
FIG. 11 shows ion exclusion chromatograms of 12 organic acids with a $CO_2$ eluent. The $CO_2$ gradient chromatogram in the middle may be compared with isocratic separations using a relatively high $CO_2$ pressure (140 psia, top) or relatively low $CO_2$ pressure (16 psia, bottom) Thermo Scientific™ Dionex™ IonPac™ ICE-AS6 column (9×250 mm); 0.5 mL/min; 160 cm Engasser; 16-140 psi (~25 mM-250 mM $CO_2$); 20 μL injection.
Figure 12:
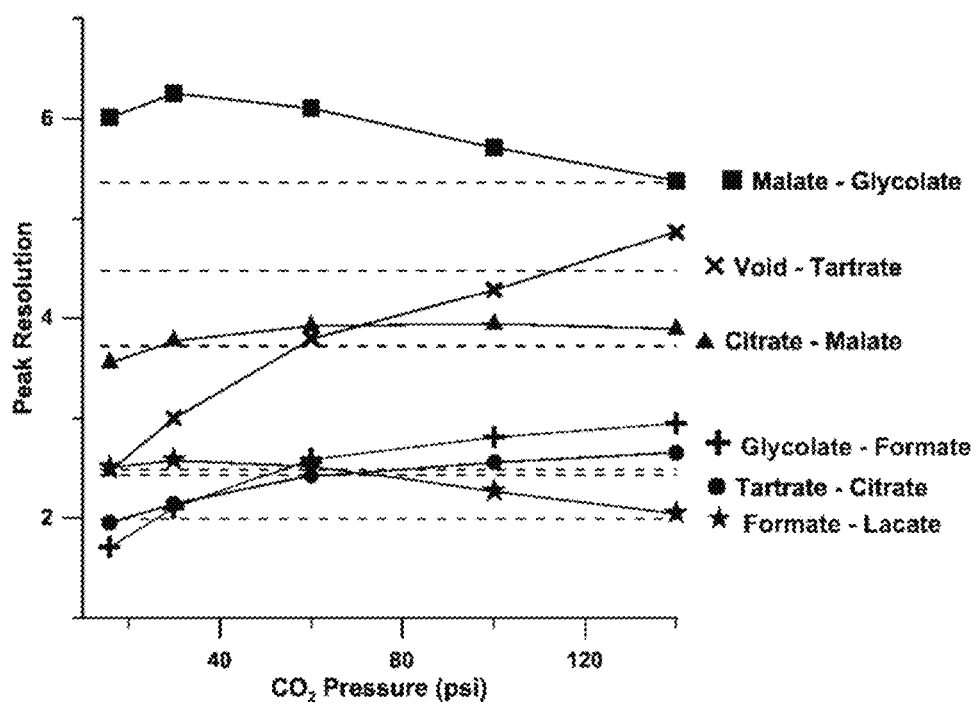
FIG. 12 is a graph showing peak resolutions for the first 6 eluting ions using isocratic $CO_2$ elution at 5 different $CO_2$ pressures ranging from 16 to 140 psia (solid symbols) compared to a gradient in the $CO_2$ pressure (the ordinate value corresponding to the dashed lines indicate the indicated peak resolution observed in the gradient chromatogram of FIG. 11).
Figure 15:
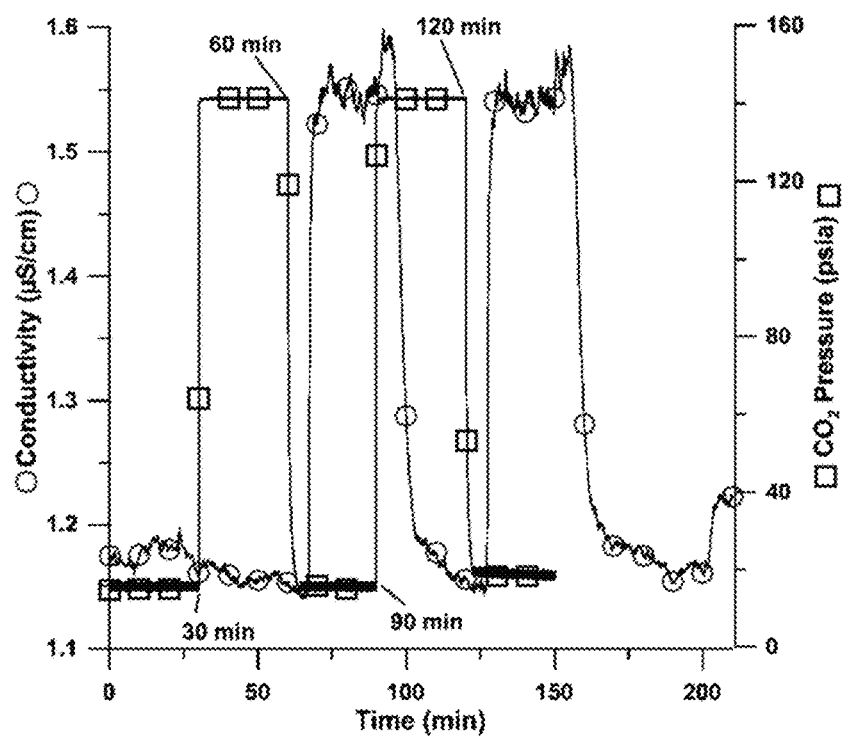
FIG. 15 is a graph illustrating a gradient delay time in ion exclusion chromatography. Because $CO_2$ fully probes the occluded volume of the resin, it takes an extended time (~32 min) for the gradient to reach the end of the column. Dionex™ IonPac™ ICE-AS6 column (9×250 mm), 0.5 mL/min, $CO_2$ pressure actuated from 14.7-140 psia, 160 cm Engasser.
Figure 16:
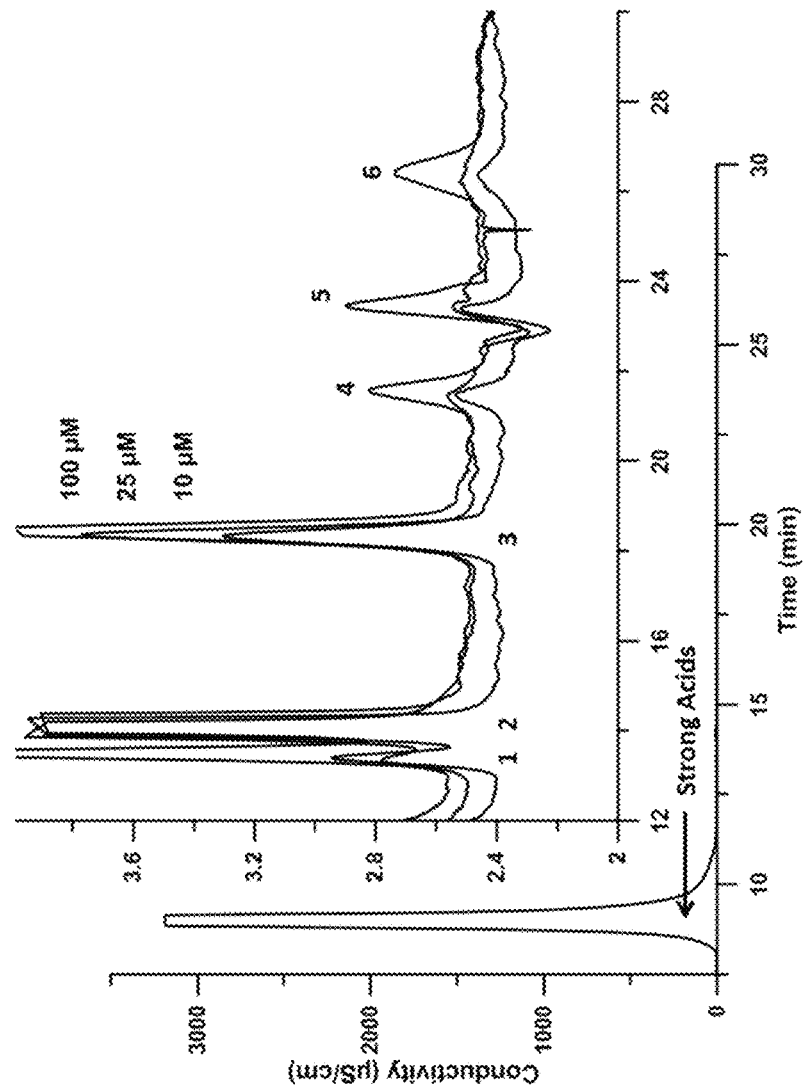
FIG. 16 is a chromatogram showing the measurement of low concentrations of organic acids in a high conductivity well water sample. The primary graph is the full scale separation while the inset contains a magnified view of just the organic acids of interest and shows how sensitive the method is using the engasser despite the overwhelming concentration of interfering strong acids. It was shown that formate and acetate were present due to contamination by the resin used to treat the sample. 1.0 mL of Sample treated with 0.5 mL of strong cation exchange resin; 100 μL Injection volume. Flow rate 0.5 mL/min; 160 cm long Engasser, 60 psi $CO_2$; (1) Lactate, (2) Formate, (3) Acetate, (4) Propionate, (5) Isobutyrate, (6) Butyrate.

If the carbonic acid concentration is high enough in the system, $H_2CO_3$ is capable of lowering the pH sufficiently to conduct efficient chromatography. Just as importantly, it can then be removed by a degasser device like the carbonate removal device (CRD) (U.S. Pat. No. 7,306,720), widely used in suppressed carbonate eluent anion exchange chromatography. In the present example, the membrane in a commercial CRD was modified by coiling it around a ⅛" rod and using a vacuum pump that drew air through a needle into a NaOH reservoir to trap any ambient $CO_2$. Chromatograms obtained in the isocratic eluent mode (constant $CO_2$ pressure on the engasser) are shown in FIG. 8. The background was only 1.644 μS/cm using up to 250 mM $CO_2$. The $CO_2$ pressure also perceptibly affects the separation (FIG. 9). Glutaric and propionic acids may have their positions reversed while fumaric acid may be eluted over a rather wide range depending on the $CO_2$ concentration. Early eluters have their resolution improved at higher applied pressures, but this comes at a loss of resolutions between peaks 7-10. This indicated a gradient in $pCO_2$ may be beneficial. Because there is a large occluded volume that $CO_2$ itself can probe, there is a very large gradient delay time (FIG. 15) (>30 minutes) suggesting that the gradient should commence even prior to sample injection (FIG. 10). The gradient separation (FIG. 11) increased the resolution (FIG. 12) for some of the early eluting ions and allowed control over where fumarate elutes as well as the retention order for glutaric and propionic acids. Early eluters were also further separated from the column void. The applicability of the method towards measuring some key weak acids in groundwater that have been identified as signatures for hydraulic fracking induced contamination has also been successfully demonstrated (FIG. 16).

Figure 13A:
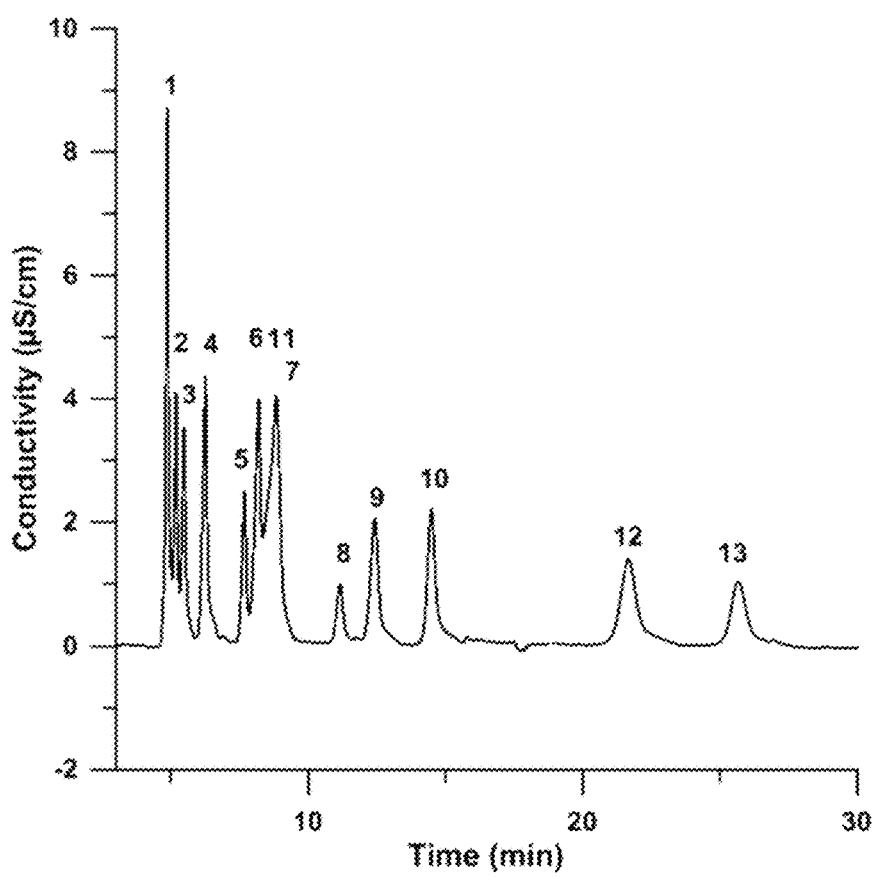
FIG. 13A shows conductivity chromatograms for a standard mixture of 13 organic acids, using a Dionex™ IonPac™ ICE-AS6 column and a flow rate of 1.0 ml/min. The inset shows the current practice, a 0.4 mM heptafluorobutyric acideluent is converted to tetrabutylammonium heptafluorobutyrate by the Themo Scientific™ Dionex™ AMMS-ICE suppressor with a detector background of ~24 μS/cm. An injection volume of 50 μL is used. The main figure shows a chromatogram according to the present invention. $CO_2$ is introduced into water with a 160 cm engasser using a pressure of 20 psi to function as an eluent. A CRD is placed between the column and the conductivity detector and is used to remove the $CO_2$ after the separation, resulting in a detector background of 1.25 μS/cm. A 20 μL injection volume is used. Compare the total time for the separation and the response (noting that in the present method less than half the sample is injected).
Figure 13B:
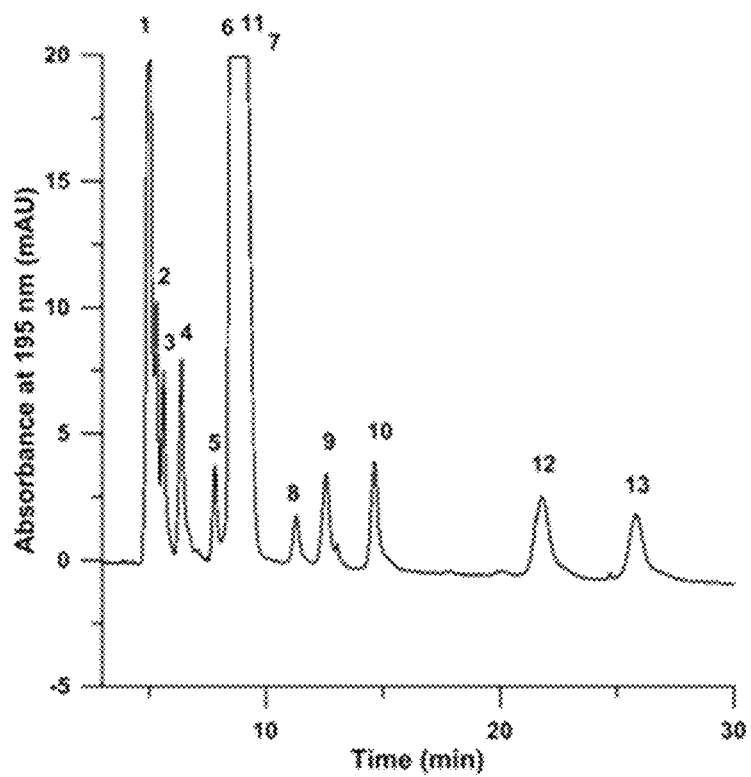
FIG. 13B depicts the same separation as FIG. 13A with the $CO_2$ eluent under identical conditions except the detector used is optical absorbance at 195 nm.

FIG. 13A and FIG. 13B show conductivity and absorbance chromatograms for a standard mixture of 13 organic acids. The current commercially standard separation is provided in the inset. The same concentrations are used, but with different temperature and injection volumes for the separation. The dip around 17.5 minutes is the $CO_2$ vacancy peak. Fumaric acid has much greater absorbance than the other weak acids which highlights the advantage of measuring using conductivity where ions will have similar response relative to their molar concentration.

Figure 14A:
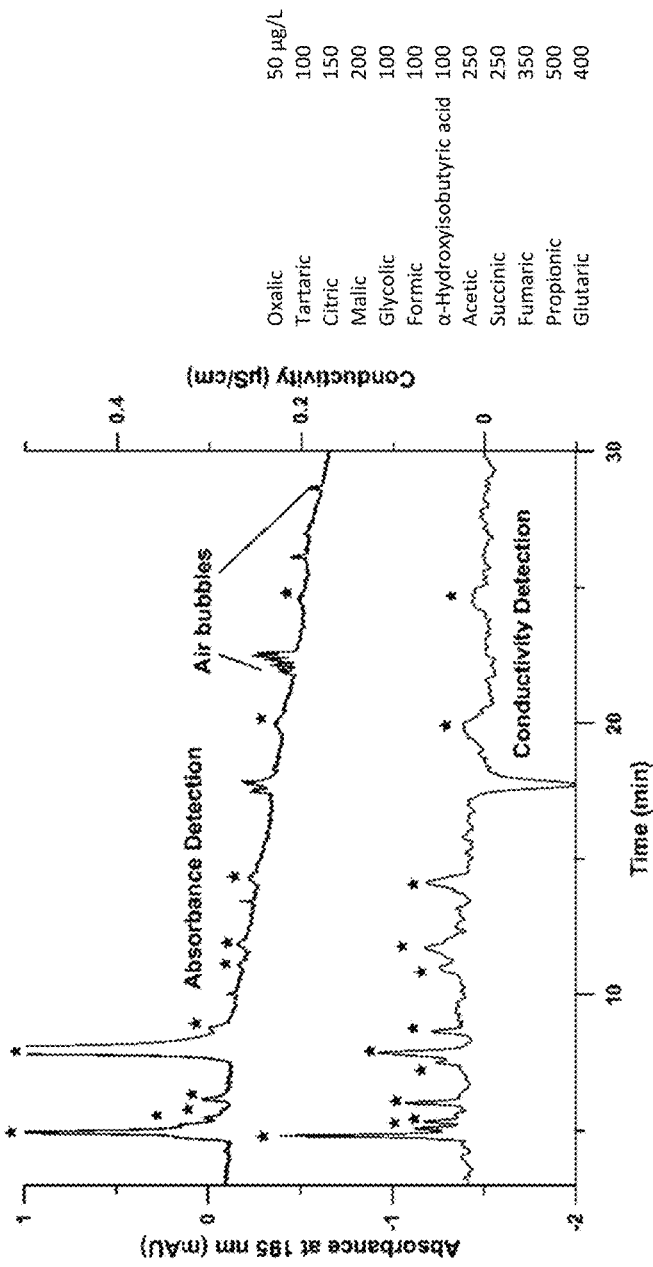
FIG. 14A compares conductivity detection to absorbance detection. $CO_2$ is removed after the separation column by a carbonate removal device (CRD). Dionex™ IonPac™ ICE-AS6 column (9×250 mm); 1.0 mL/min; $CO_2$ pressure=5 psia; 160 cm Engasser; 20 μL sample loop; 40° C.
Figure 14B:
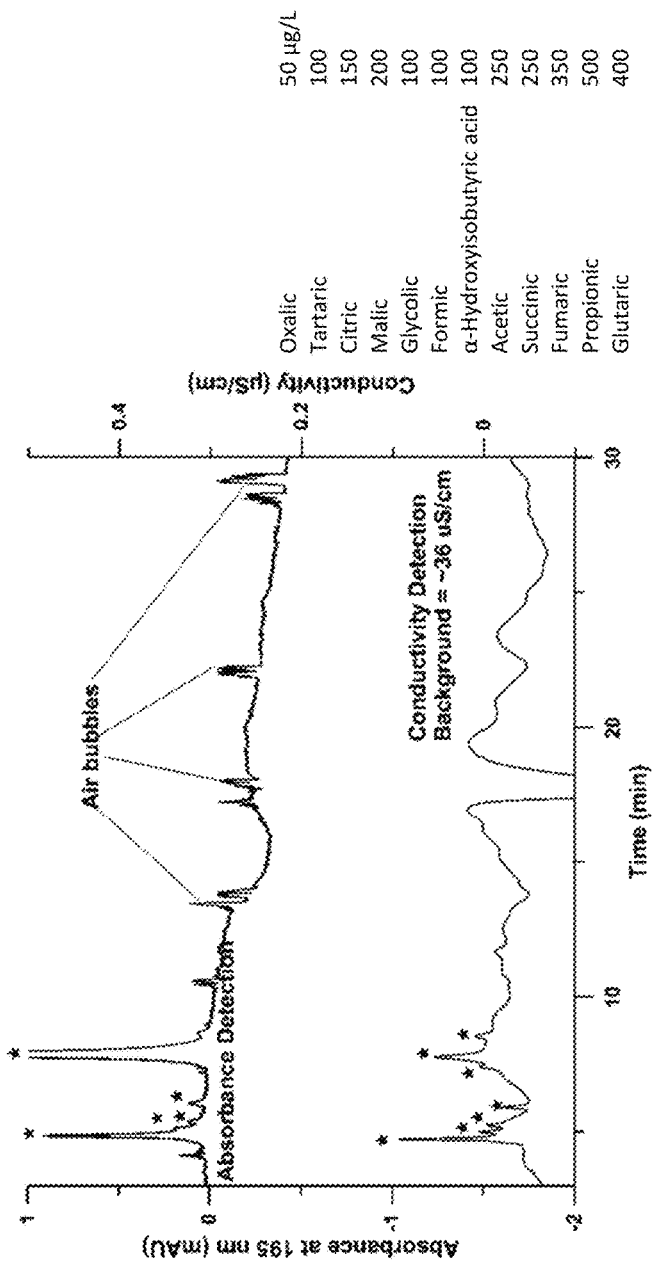
FIG. 14B is a chromatogram showing the separation without carbon dioxide removal (without the CRD). Many of the ions are not identifiable with either absorbance or conductivity without the CRD, showing the merits of removing the eluent background. Dionex™ IonPac™ ICE-AS6 column (9×250 mm); 1.0 mL/min; $CO_2$ pressure=5 psia; 160 cm Engasser; 20 μL injection volume; 40° C.

Conductivity provided better results at low concentrations compared to absorbance. Some residual $CO_2$ or other dissolved gas caused air bubbles to develop to which the absorbance detector was very sensitive. Subsequently more efficient $CO_2$ removal was accomplished by using narrower bore CRD tubing with the tubing coiled around a ⅛" rod. FIG. 14B shows the separation without the CRD. In neither absorbance nor conductivity are any of the ions identifiable without $CO_2$ removal.

3.2 Ion Exchange Chromatography

Figure 17:
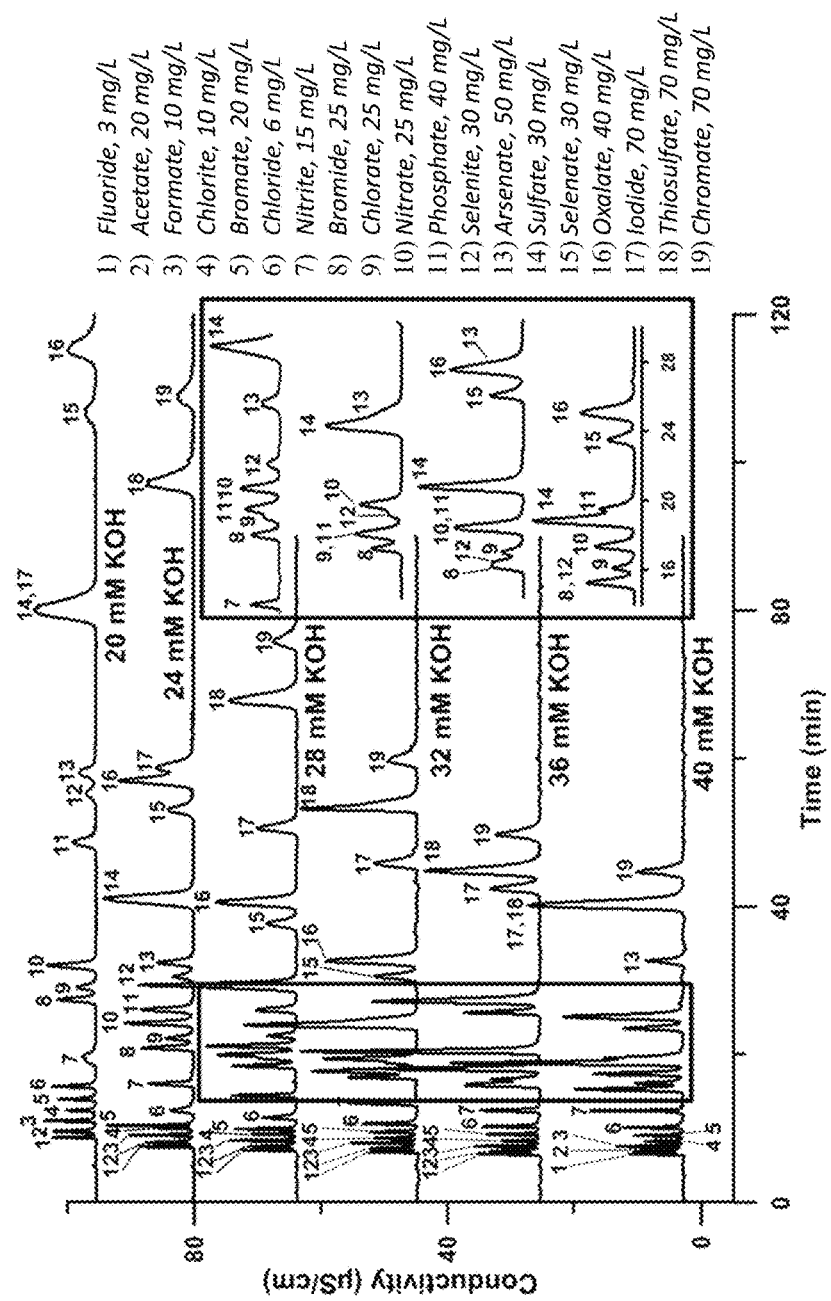
FIG. 17 is a plurality of chromatograms showing the separation of ions on a Dionex™ IonPac™ 4 mM i.d. AS-9HC column using electrodialytic KOH generation and $CO_2$ Engasser. $CO_2$ pressure was held constant at 145 psi (~15.4 mM) $CO_2$ and the KOH concentration were varied from 20 mM to 40 mM. The rectangular inset shows a region where the elution behavior is strongly dependent upon the eluent composition. Flow Rate 0.5 mL/min; Engasser length 5.5 cm; 20 μL injection volume.
Figure 18:
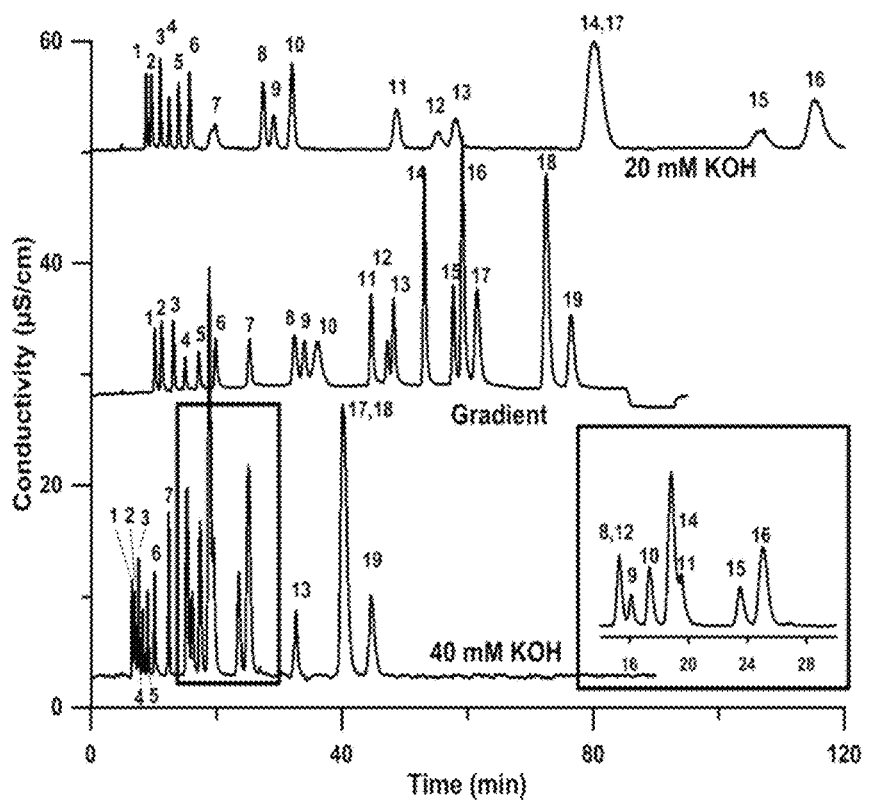
FIG. 18 reproduces the top and bottom traces from FIG. 17. The middle trace utilizes a bicarbonate-carbonate gradient and results in a more attractive separation (i.e., faster analysis time) than either the top or the bottom chromatogram.
Figure 19A:
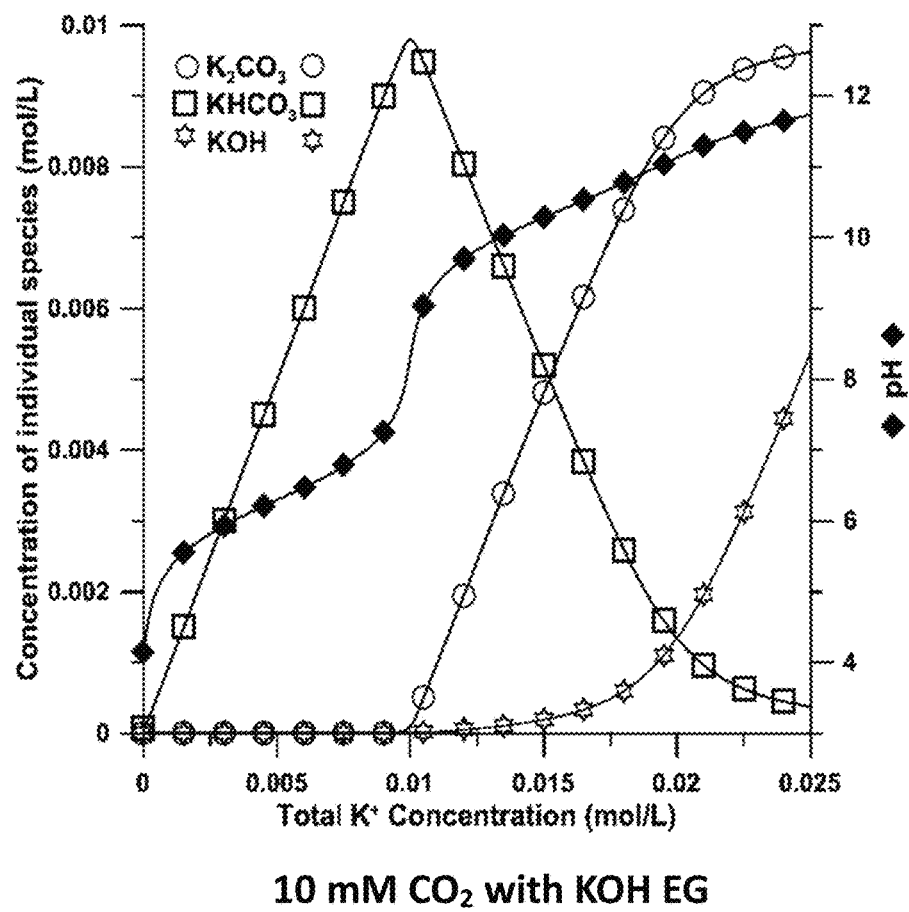
FIG. 19A shows the distribution of species ($KHCO_3$, $K_2CO_3$, KOH) in the eluent as $CO_2$ is held constant at a total dissolved concentration of 10 mM to maintain a stable constant background while the KOH concentration was altered from 0 to 25 mM. A large eluent pH range (~4-12) is possible.
Figure 19B:
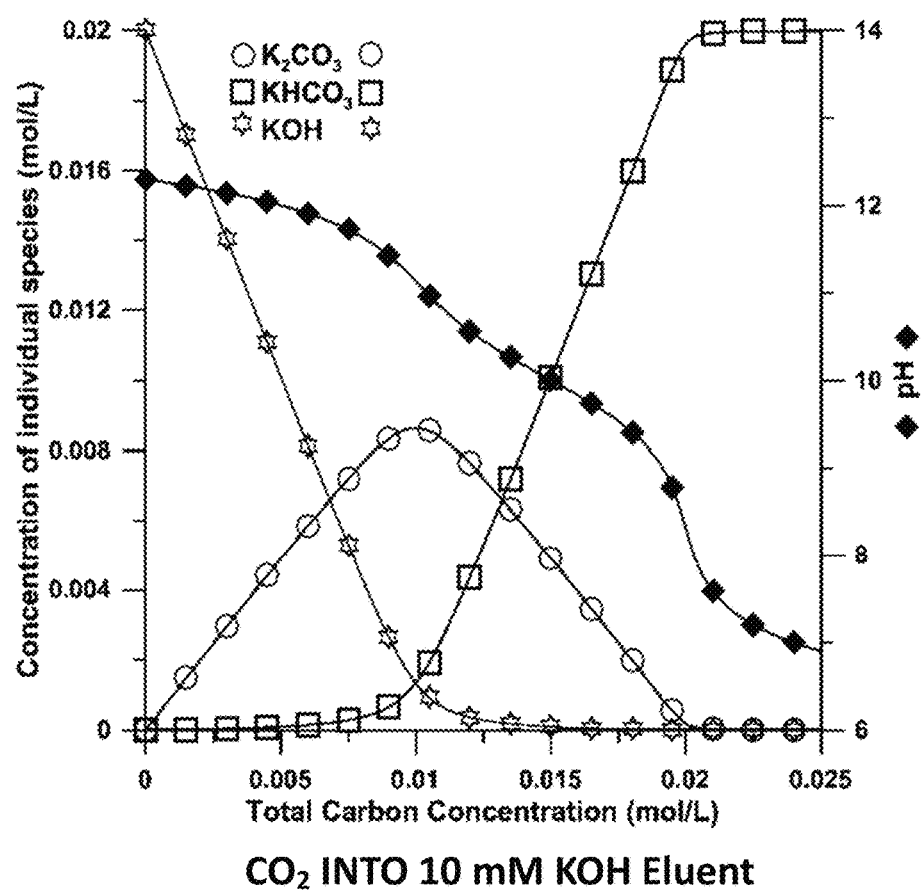
FIG. 19B similarly shows the distribution of species where a constant 10 mM KOH is used as the influent to the engasser and the total carbonate carbon content is varied from 0 to 25 mM. The total pH span possible is less than that in FIG. 19A.
Figure 20:
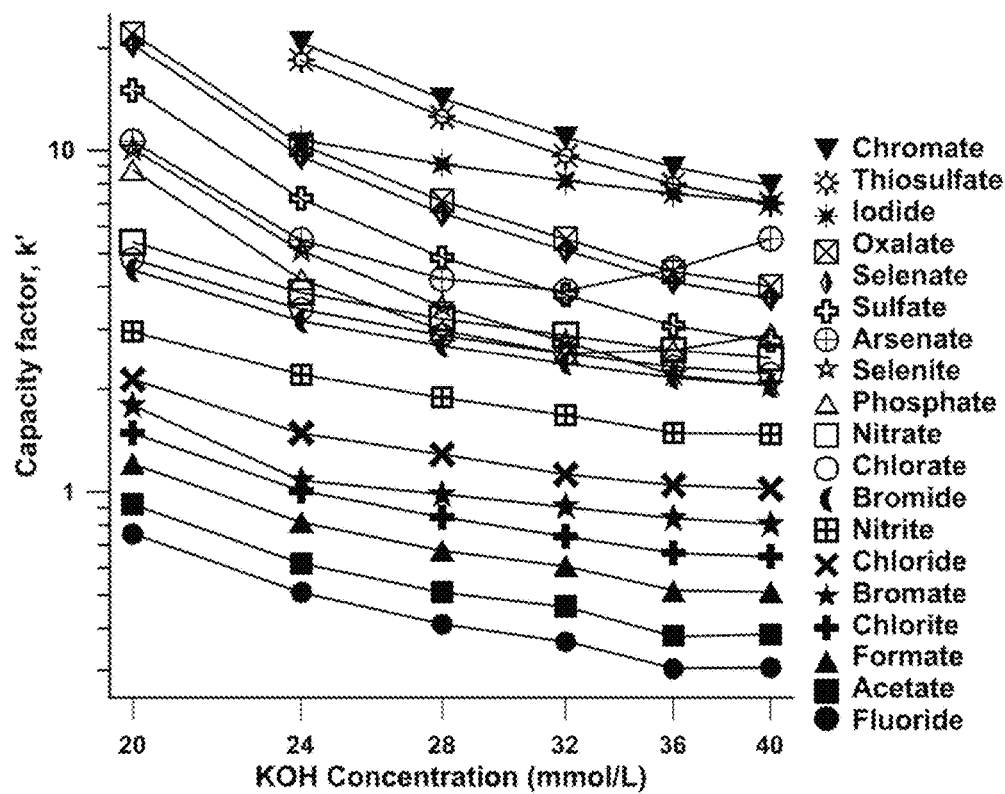
FIG. 20 is a graph showing capacity factor (k') dependence of ions based on the KOH concentration ranging from 20 to 40 mM while $CO_2$ engasser (5.5 cm) pressure is held constant at 145 psi (~15.4 mM total carbonate). Corresponding separations are shown in FIG. 17. Arsenate and phosphate retention increased as the pH is raised due to their increasing charge. The other ions showed a decreasing capacity factor with increasing KOH concentration. Both axes have logarithmic scaling. The curvature is caused due to the transition from bicarbonate to carbonate.
Figure 21:
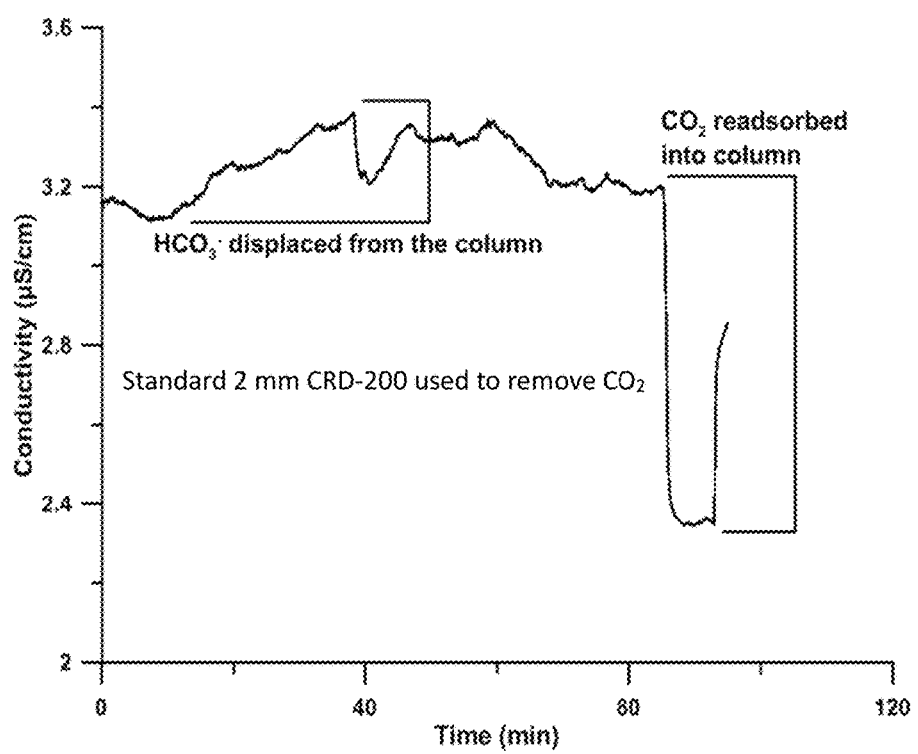
FIG. 21 is a graph showing the effect of the carbonate gradient on the background conductance. 5.5 cm Engasser pressure is maintained constant at 145 psi $CO_2$ (~15.4 mM) while the KOH concentration is changed with time as follows: 0-5 min 18 mM KOH; 5-35 min 18-23 mM KOH; 35-55 min 23-40 mM KOH; 55-80 min 40 mM KOH; 80-80.5 min 40-18 mM KOH; 80.5-95 min 18 mM KOH. A rise can be seen where $HCO_3^-$ is displaced by $CO_3^{2-}$. Conversely, a dip is caused as $CO_2$ is resorbed back onto the column to make $HCO_3^-$. Use of higher concentrations of $CO_2$ in the eluent is advantageous for faster re-equilibration of the column. Flow rate 0.5 mL/min; Dionex™ IonPac™ AG/AS-9HC 4 mm ø column set.

Very high purity carbonate eluents with low background conductance can be easily generated without the need to prepare solutions or manually adjust the pH. By placing an eluent generator (and degasser) prior to the engasser it is possible to make solutions of $HCO_3^-/CO_3^{2-}/OH^-$ of varying strength and pH. Separation was performed on a Dionex™ IonPac™ AS-9HC column prior to suppression and removal of $CO_2$ through the aforementioned modified CRD. Speciation models are provided in FIG. 19A and FIG. 19B that illustrate solution composition and pH. Because of the pH control and difference in selectivity between $HCO_3^-$ and $CO_3^{2-}$, carbonate based elution still offers some advantages over the hydroxide eluent ion chromatography and will likely see increasing use as a new low noise carbonate suppressor has been developed (U.S. Patent Application Publication No. U.S.20160041133A1). Isocratic separation with carbonate eluents made in line can be seen in FIG. 17 for 19 different anions. FIG. 20 shows the capacity factor dependence upon the hydroxide concentration. As the concentration increases, so does the pH which increases the charge on phosphate and arsenate and thus their retention. Such selectivity choices for polyvalent weak ions are lost when using a pure hydroxide gradient. A hydroxide gradient using the eluent generator may be produced to improve the separation (FIG. 18). The gradient consisted of isocratic elution using 18 mM KOH from 0-5 minutes followed by a linear ramp from 18-23 mM KOH during 5-35 min, then another linear ramp from 35-55 min in which the KOH was raised from 23-40 mM, then the KOH was held constant at 40 mM from 55-80 minutes, then the system was allowed to re-equilibrate with 18 mM KOH for 15 minutes. Of note is the low background and the lack of baseline drift/shift (FIG. 21). There is a slight increase in conductivity during the start of the gradient as $HCO_3$ is displaced by $CO_3^{2-}$. Then during the re-equilibration stage the conductivity decreases as $CO_2$ is readsorbed back onto the stationary phase as $HCO_3^-$.

3.4 Chiral Amine Separation

Figure 22:
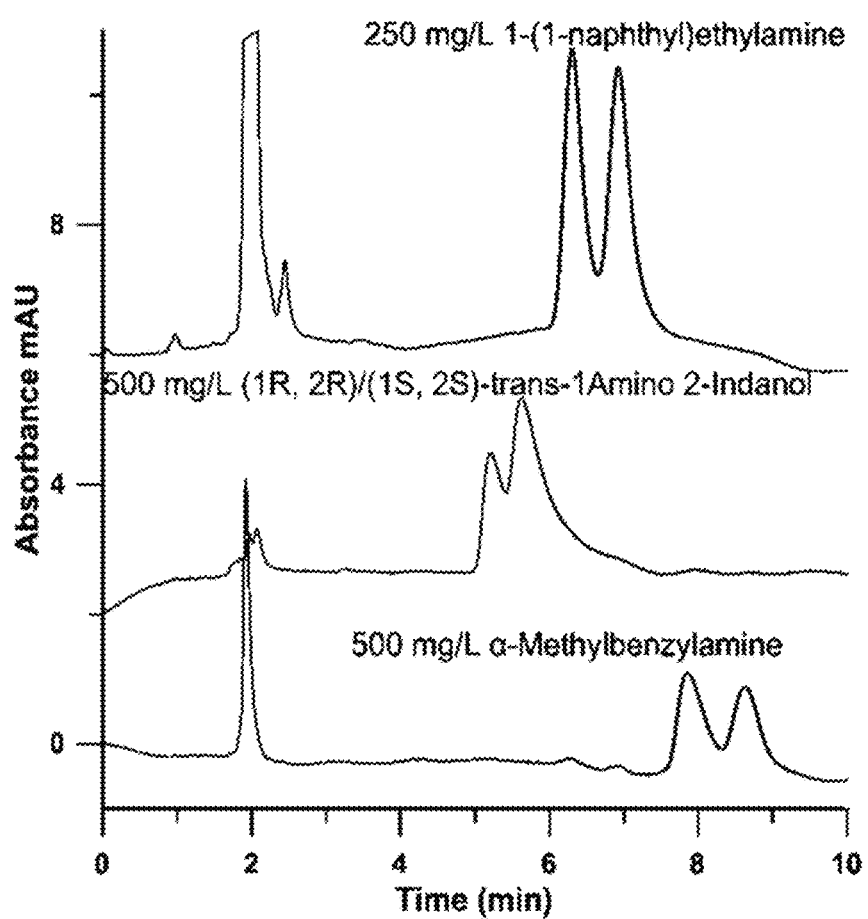
FIG. 22 shows separations of 3 different racemic mixtures of chiral amines using an eluent containing 60:40 acetonitrile:MeOH, 0.05% triethylamine that goes through a 160 cm Engasser operating with 60 psi $CO_2$. A chiral stationary phase (LARIHC CF6-P (4.6×150 mm) column with 5 μm fully porous particles (a chiral stationary phase (CSP) with an alkyl derivatized cyclofructan 6 chiral stationary phase, which is commericially available from AZYP, LLC) was used. The injection volume was a 20 μL injection loop and optical absorbance detection at 254 nm was used. Note that these drugs/drug precursors can be obtained in pure form after separation as all eluent components are volatile.
Figure 23:
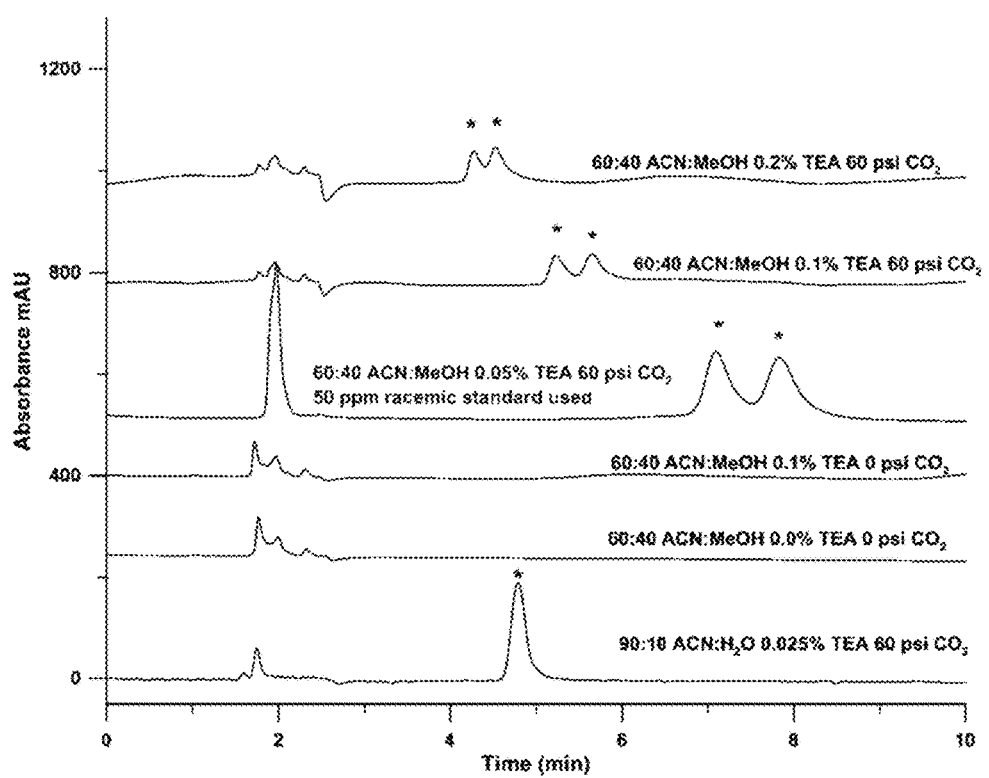
FIG. 23 is a series of chromatograms showing different separation conditions tested for the separation of the chiral amine 1-(1-naphthyl)ethylamine. Effective separation was not achieved in more heavily aqueous media operating in a reverse phase mode and use of even 10% water resulted in no chiral selectivity. HILIC using polar organic solvents was found to separate the compounds. Triethylamine was required and no elution occurred without it. Other amines such as ammonia and trimethylamine were too strong, and were ineffective. According to a method of the invention, these amines could be separated under 60:40 ACN:MeOH and 0.05-0.2% triethylamine. Use of an eluent formed by introduction of gaseous $CO_2$ into the eluent precursor/eluent is critical for elution. Other conditions were similar to those described for FIG. 22, except detection at 225 nm. Sample contained 25 mg/L racemic 1-(1-naphthyl)ethylamine.

Chiral amines are most often separated by an ion pairing effect using an acid as the pairing agent. Here, chiral amines were separated using $CO_2$ as the pairing agent. This may be particularly advantageous for large scale separations where cleanup from the pairing agent ($HClO_4^-$) can be difficult or costly. FIG. 22 shows the separation of 3 different chiral amines on a LARIHC CF6-P (4.6 mm i.d.×15 cm, 5 μm fully porous particles, AZYP, LLC). No separation was found to occur without the presence of $CO_2$ or a base such as triethylamine (FIG. 23).

3.5 Amino Acid Separation

Figure 25A:
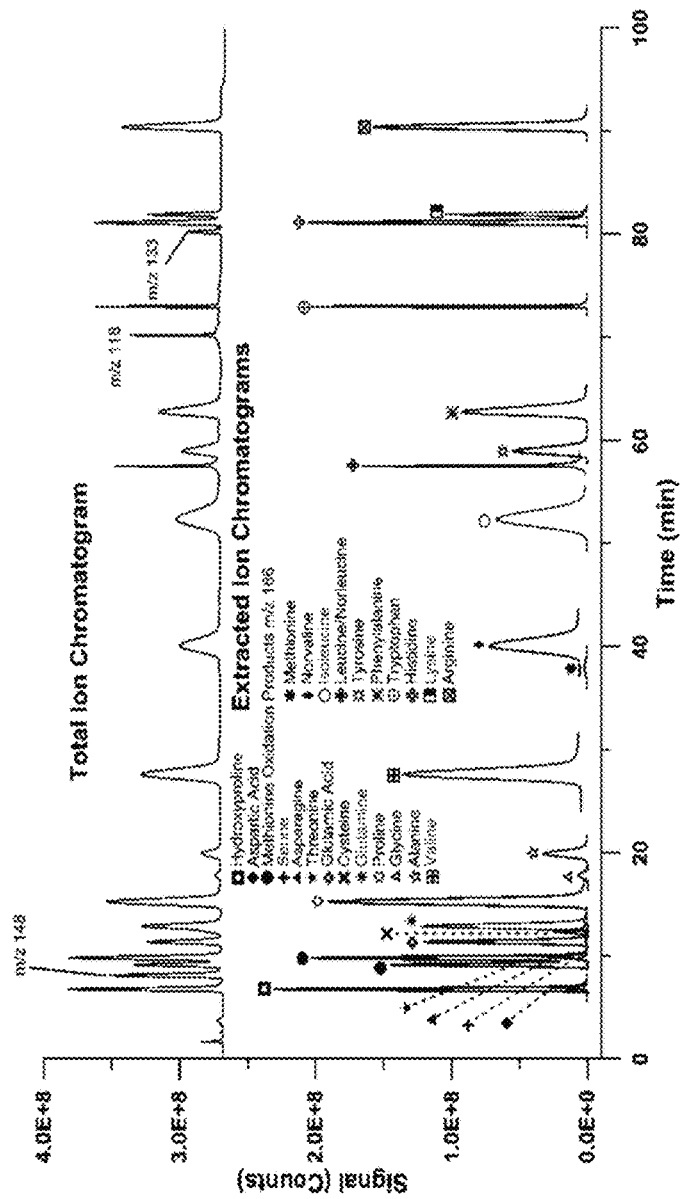
FIG. 25A shows a chromatogram of 23 amino acids separated by cation exchange on Dionex™ IonPac™ CG/CS-3 4 mmø column set. The top trace is the total ion chromatogram from a mass spectrometer for all the amino acids. The lower traces are extracted ion chromatograms at the appropriate mass to charge ratio of the individual amino acids. All amino acids are 100 μM in concentration. The $NH_3$ Engasser was 25 cm in length and the $CO_2$ Engasser was 40 cm long. The Engasser influent was 20 mM formic acid flowing at 1 mL/min.
Figure 25B:
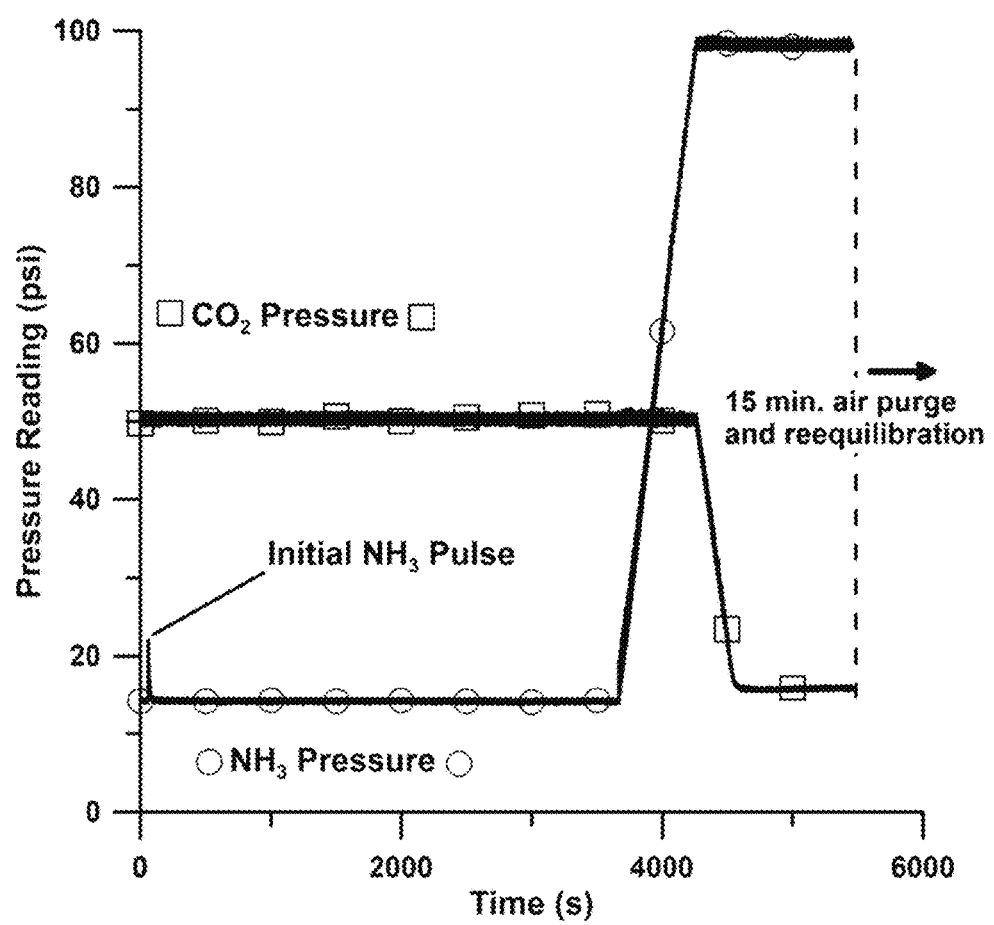
FIG. 25B shows the pressure sensor readout out for the gradient amino acid separation performed in FIG. 25A. An air purge was used to remove $NH_3$ from the engasser to achieve a lower concentration of $NH_4^+$ in the eluent. During the air purge, the formic acid converts the column from $NH_4^+$ to $H^+$. $H^+$ is a weaker eluent than $NH_4^+$. The initial separation is performed isocratically using formic acid. A brief $NH_3$ pulse is applied to fill the Engasser with a low pressure of $NH_3$ and then the vent solenoid is opened. The column then is converted back to $NH_4^+$. This creates a transition zone. Some amino acids are eluted easily by the $NH_4^+$ and not $H^+$ and therefore concentrate in the transition zone. To prevent this, a vacuum can be applied to the gas outlet to allow lower concentrations of $NH_3$ without removing it entirely as occurs in the air purge.

The separation and determination of amino acids have been and continue to be important. Amino acids have both cationic and anionic functionalities. The net charge is dependent on the pH. This allows the use of cationic or anionic separation columns. If an anion exchange column is used, elution is first carried out using $HCO_3^-$ which is a weak eluent before switching to $CO_3^{2-}$, a much stronger eluent. Analytes tend to concentrate in the zone between the two as is observed with phenylalanine, glutamine and arginine in FIG. 26A. (It is possible to operate with ammonium carbonate entirely, just go from very low to higher concentrations.) A cation exchange column on the other hand allows a single eluent ion: $NH_4^+$. In addition there are other volatile weak acids that can extend the pH range even lower (e.g. formic acid). Similar volatile bases are not as readily available. A mass spectrogram shows a separation of a number of amino acids on a Dionex™ IonPac™ 4 mm inner diameter column set are shown in FIG. 25A. $NH_4^+$ was found to be a fairly strong eluent ion on this particular column. To reduce the concentration at the beginning of a gradient separation, the Engasser was first purged with air. 20 mM formic acid in the eluent then converted the column into the weaker $H^+$ form and served as the primary eluent at the start of the separation. The gradient program pressure readback can be seen in FIG. 25B. This however creates the same problem observed with the anion column where there is a transition zone in which analytes may concentrate, though the effect was less pronounced in going from $H^+$ to $NH_4^+$ than from $HCO_3^-$ to $CO_3^{2-}$. Leucine and norleucine were found to elute in the transition zone as seen in FIG. 25A. The transition was created using a controlled brief pulse of $NH_3$ to the Engasser shortly after the start of the run. The top trace is the total ion chromatogram of all the monitored mass to charge (m/z) signals. Extracted signals at the relevant m/z for each amino acid are provided in the lower traces to identify the amino acid. Because $NH_3$ and $CO_2$ are both volatile and of high purity, coupling to mass spectrometry is simple.

Figure 26A:
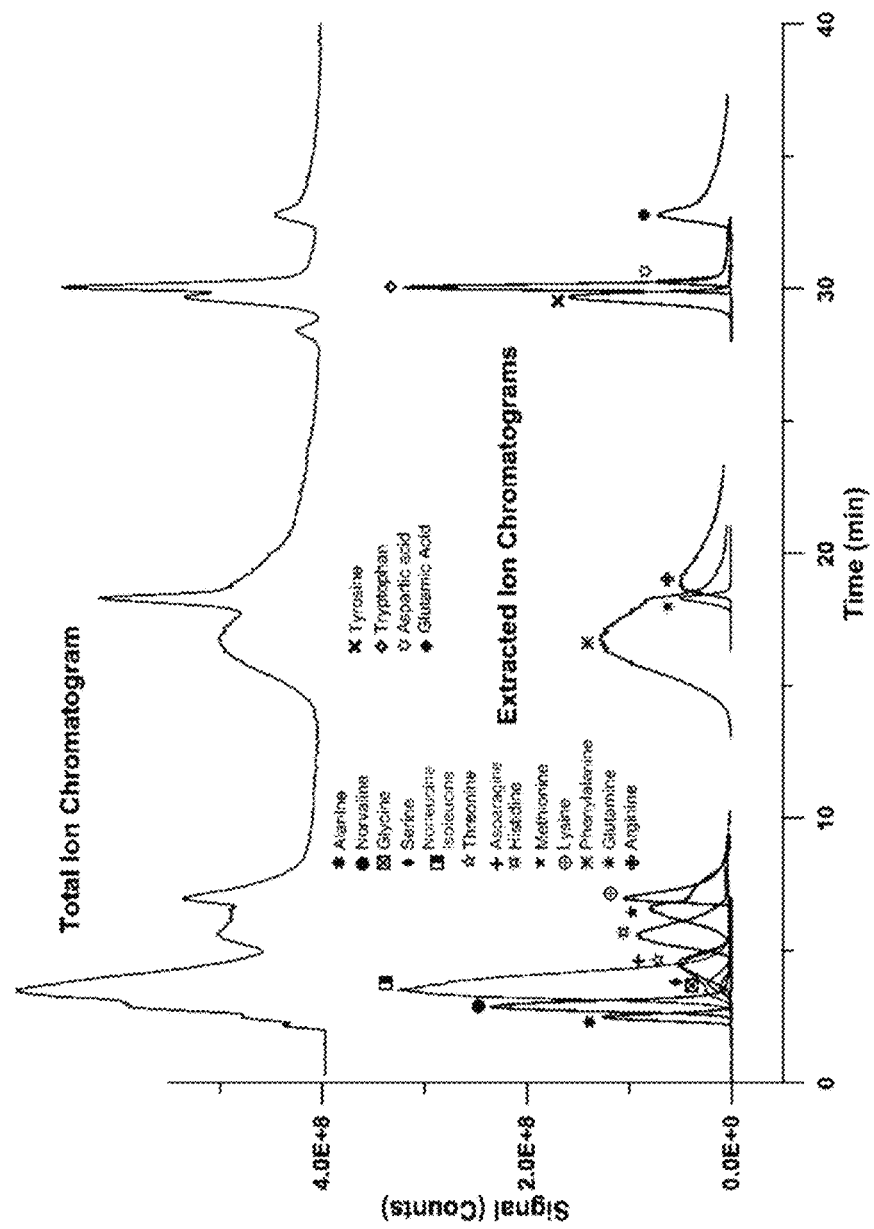
FIG. 26A is similar to FIG. 25A, except the separation is conducted on an anion exchange column and the mixture contains 18 amino acids. Obviously the cation exchange mode provides for a better separation. The top trace is the total ion chromatogram from a mass spectrometer for all the amino acids. The lower traces are extracted ion chromatograms at the appropriate mass to charge ratio of the individual amino acids. All amino acids are 100 µM in concentration. The $NH_3$ Engasser was 25 cm in length and the $CO_2$ Engasser was 40 cm long. The eluent contained 20 mM Formic Acid flowing at 1 mL/min.
Figure 26B:
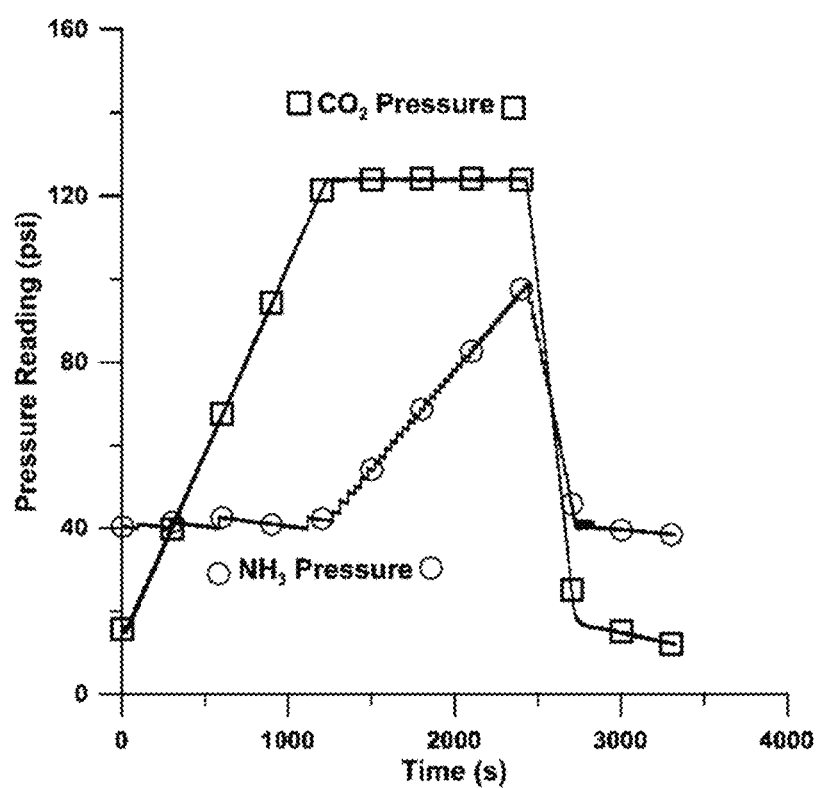
FIG. 26B is a graph showing the pressure sensor readouts of the $NH_3$ and $CO_2$ gradient used in FIG. 26A. The indicated pressure is in pounds per square inch absolute (psi).

When using an anion exchange column for amino acid separation as shown in FIG. 26A, phenylalanine was observed to elute where the gradient is transitioning from bicarbonate to carbonate so it is focused at the transition front. The same is true of arginine. The column was an IonPac PA-10 2 mm. The flow was split 15× to dilute the concentration of the eluent but still most of the amino acids elute very early. The pressure gradient is shown in FIG. 26B. The top trace in the chromatogram is the total ion chromatogram obtained on a mass spectrometer. The lower traces are marked with symbols and are the extracted ion chromatograms at the relevant m/z ratio to identify the eluting amino acids.

Figure 27:
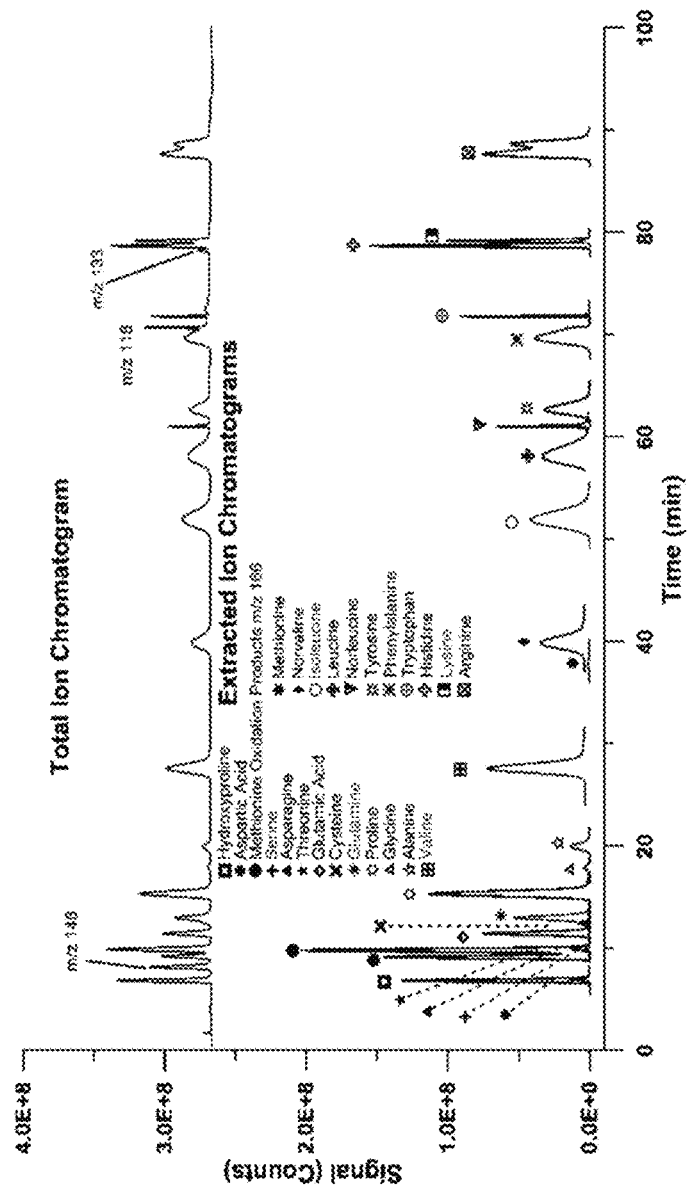
FIG. 27 shows a chromatogram for the separation of 23 amino acids, Dionex™ IonPac™ CG/CS-3 4 mmø column set. Separation is identical to that performed in FIG. 25A using the gradient shown in FIG. 25B except that no $CO_2$ was used during the separation. The top trace is the total ion chromatogram from a mass spectrometer for all the amino acids. The lower traces are extracted ion chromatograms at the appropriate mass to charge ratio of the individual amino acids.
Figure 28:
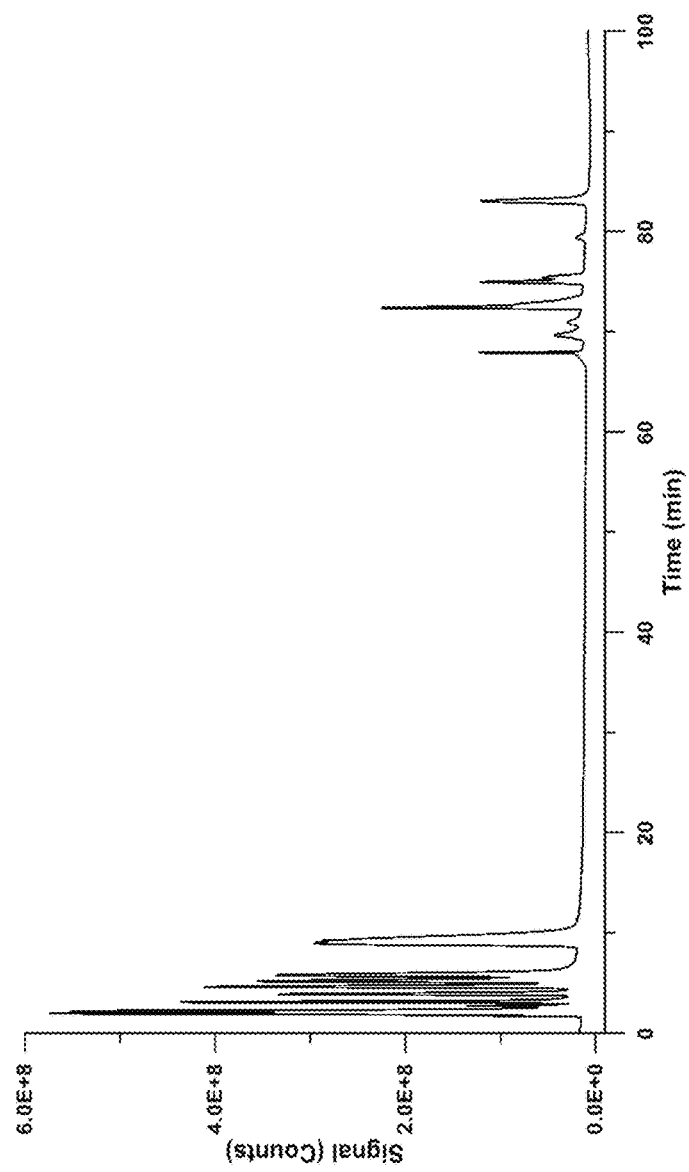
FIG. 28 shows a chromatogram for the separation of 23 amino acids, Dionex™ IonPac™ CG/CS-3 4 mmø column set. Separation is identical to that performed in FIG. 25A using the gradient shown in FIG. 25B except that no formic acid was used during the separation. Without formic acid to lower the pH and render the amino acids cationic, all but the most basic amino acids are poorly retained and poorly resolved.
Figure 29:
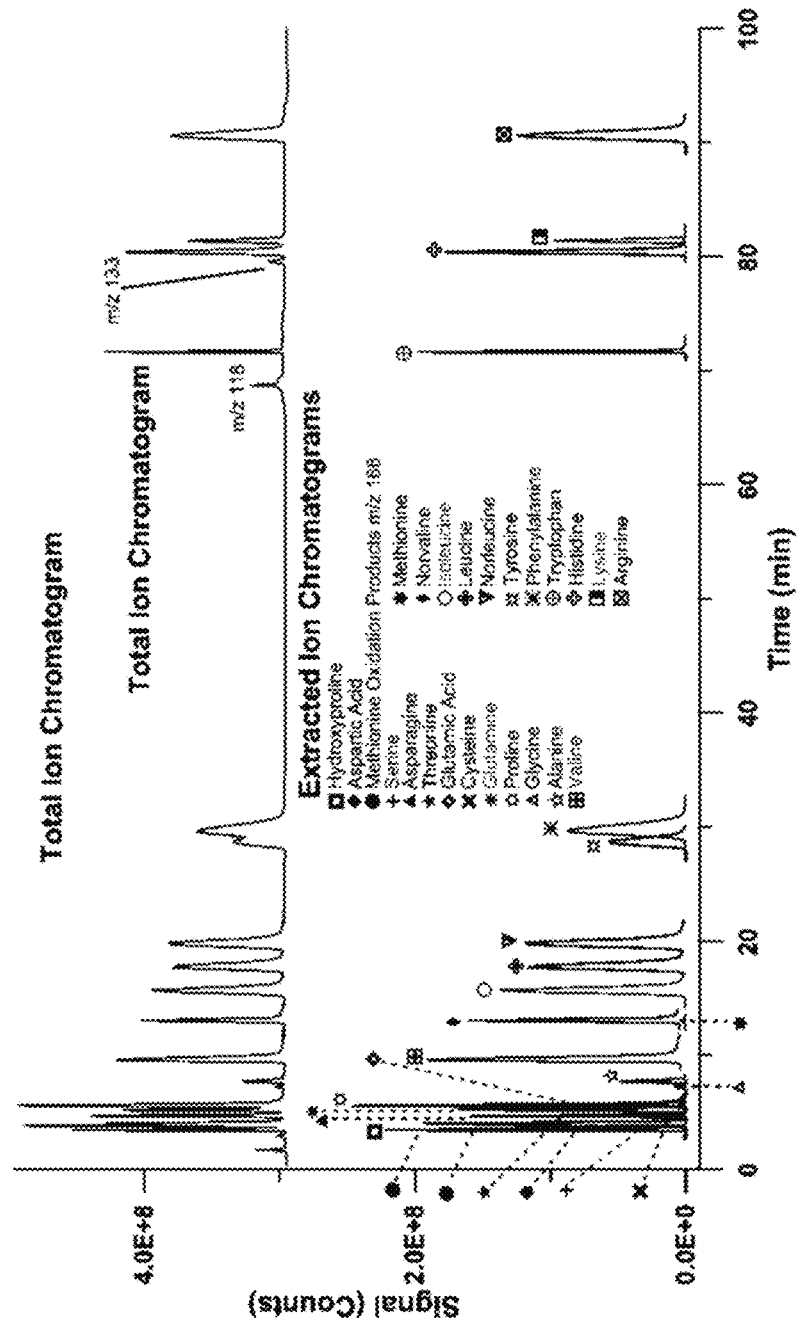
FIG. 29 shows a chromatogram for the separation of 23 amino acids Dionex™ IonPac™ CG/CS-3 4 mmø column set. Separation is identical to that performed in FIG. 25A using the gradient shown in FIG. 25B except that no air purge was used to lower the $NH_3$ concentration in the engasser prior to the separation. The top trace is the total ion chromatogram from a mass spectrometer for all the amino acids. The lower traces are extracted ion chromatograms at the appropriate mass to charge ratio of the individual amino acids. While many of the acids are now unresolved and elute in 5 minutes, it can be see that isoleucine, leucine, and norleucine are well resolved and elute in a reasonable time unlike in FIG. 25A. Tyrosine and phenylalanine however are significantly less resolved than before. A greater dynamic range in the $NH_3$ pressure, especially at the low end, can be achieved with a vacuum on the engasser outlet.
Figure 30:
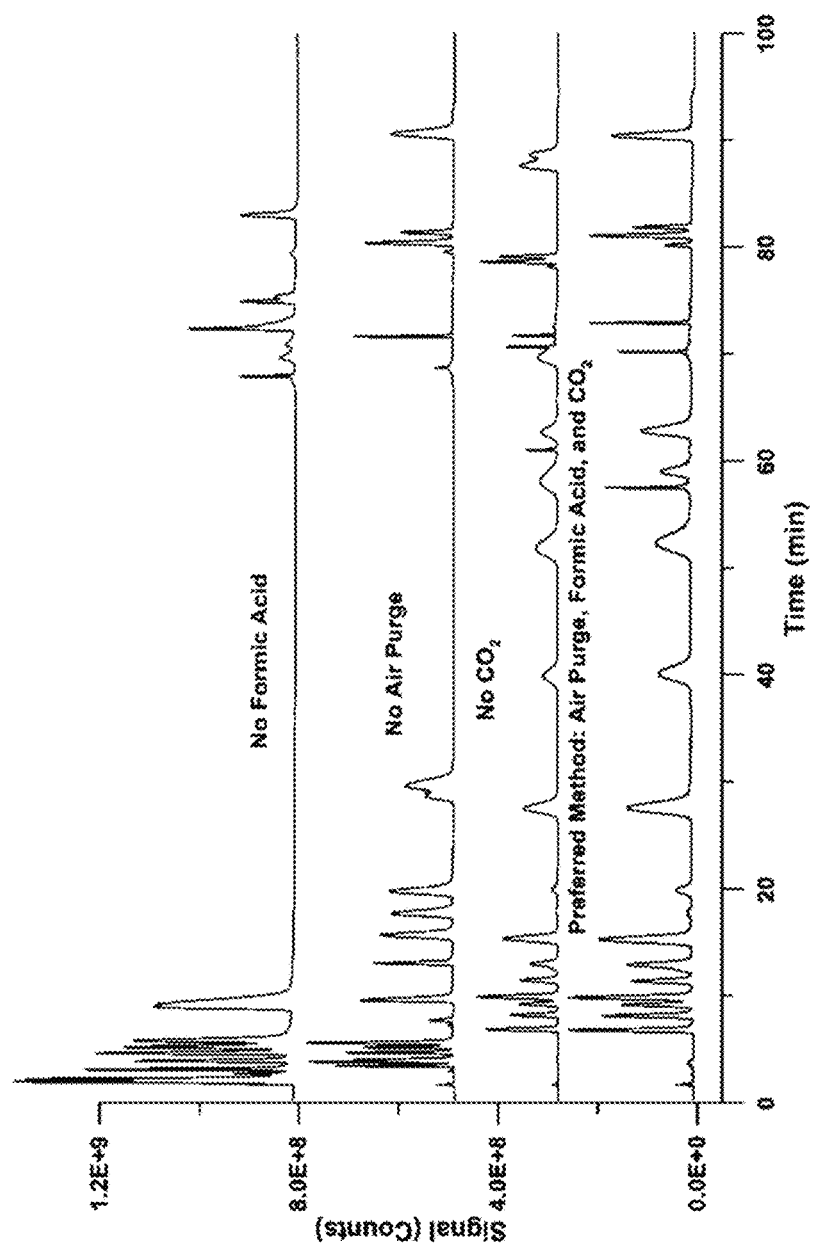
FIG. 30 is a series of chromatograms showing a comparison of ion chromatograms of various gradient methods tested. The $CO_2$—$NH_3$-formic acid system allowed the best separation. The additional $CO_2$ created a greater buffered region and allowed higher ionic strengths so that elution of late ions provided more efficient (e.g., sharper, narrower) peaks.

The role of $CO_2$, formic acid, and air purge were explored and are provided in FIG. 27, FIG. 28, and FIG. 29 respectively. While the separation without $CO_2$ is still of some use, its absence reduces the upper ionic strength limit and thus elution strength at a given pH, as well as buffering in neutral to alkaline pH. This is expected to play a more crucial role with larger peptides and biomolecules. Formic acid was found to be necessary to lower the pH below that obtained using only $CO_2$ in order to increase retention of amino acids. The air purge as described previously lowers the $NH_3$ concentration and allows elution by $H^+$, a weaker eluent. FIG. 30 compares all 4 separation conditions.

3.6 Monoclonal Antibody Separation

Figure 31:
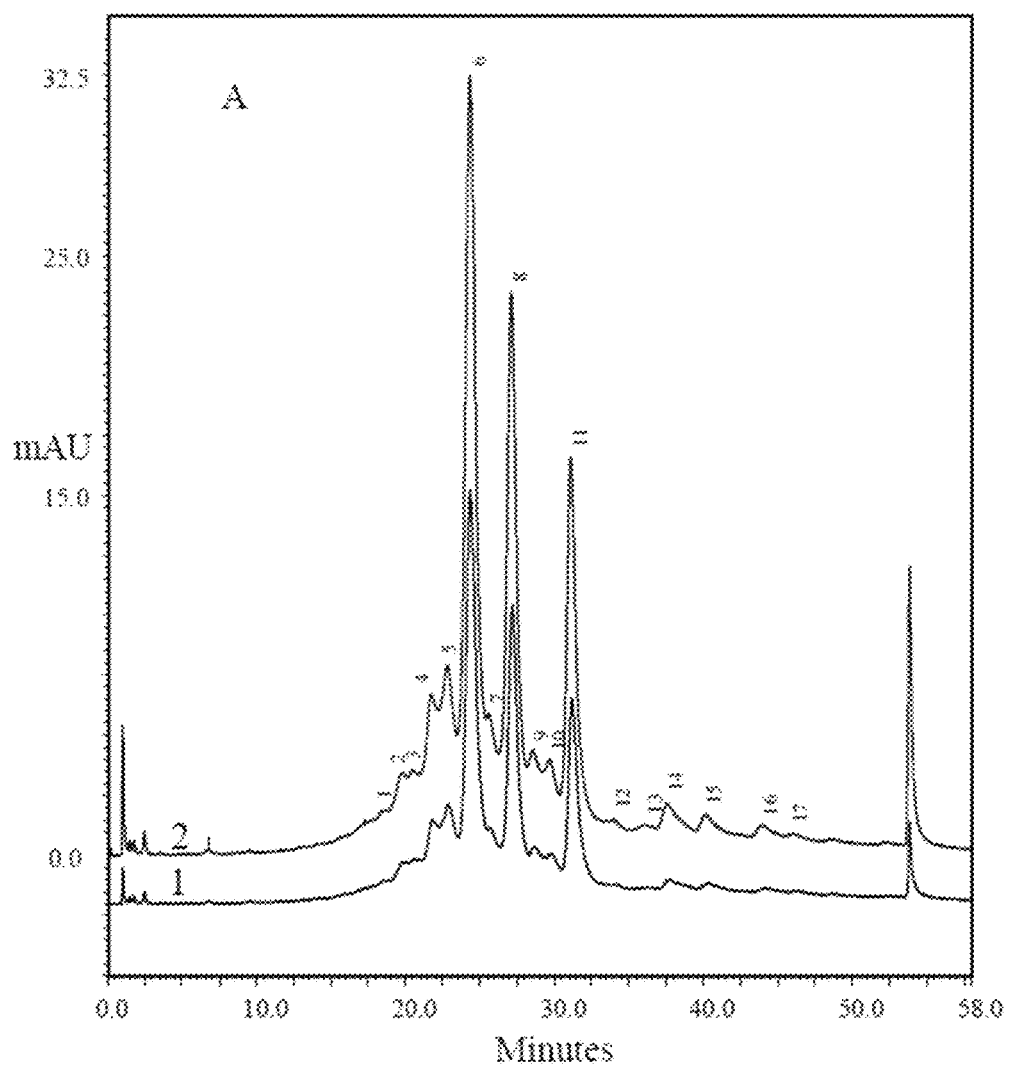
FIG. 31 is a chromatogram showing separation of monoclonal antibody variants using 2-(N-morpholino)ethanesulfonic acid (MES) eluent. Column: Thermo Scientific™ Dionex™ MAbPac™ SCX-10, 10 µm, 4×250 mm; Eluent: A; 20 mM MES+60 mM NaCl pH 5.6; B: 20 mM MES+300 mM NaCl, pH 5.6; Gradient: 15-36.44% B in 50 min; Flow Rate: 1 mL/min; Temp: 30° C.; Sample: MAb, 5 mg/mL; 1) Sample 1: 25 µg; 2) Sample 2: 50 µg; Detection: 280 nm; Peak: 1-5: Acidic variants; Peaks 6, 8, and 11: C-terminal Lys variants.
Figure 32:
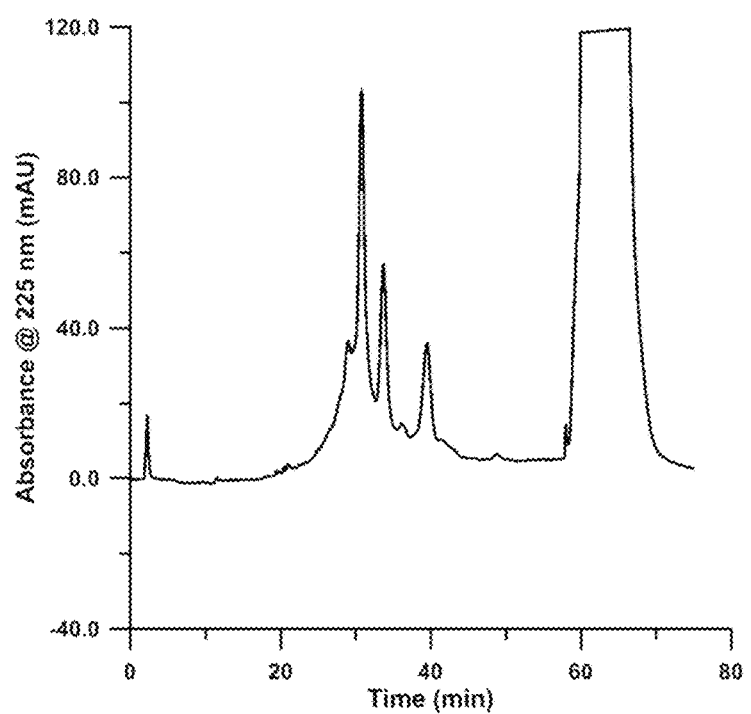
FIG. 32 is a chromatogram of the same sample and on the same column as in FIG. 31 except a gradient eluent system of $NH_3$—$CO_2$ is used for separation; this will allow the antibodies to be recovered in pure form.
Figure 33:
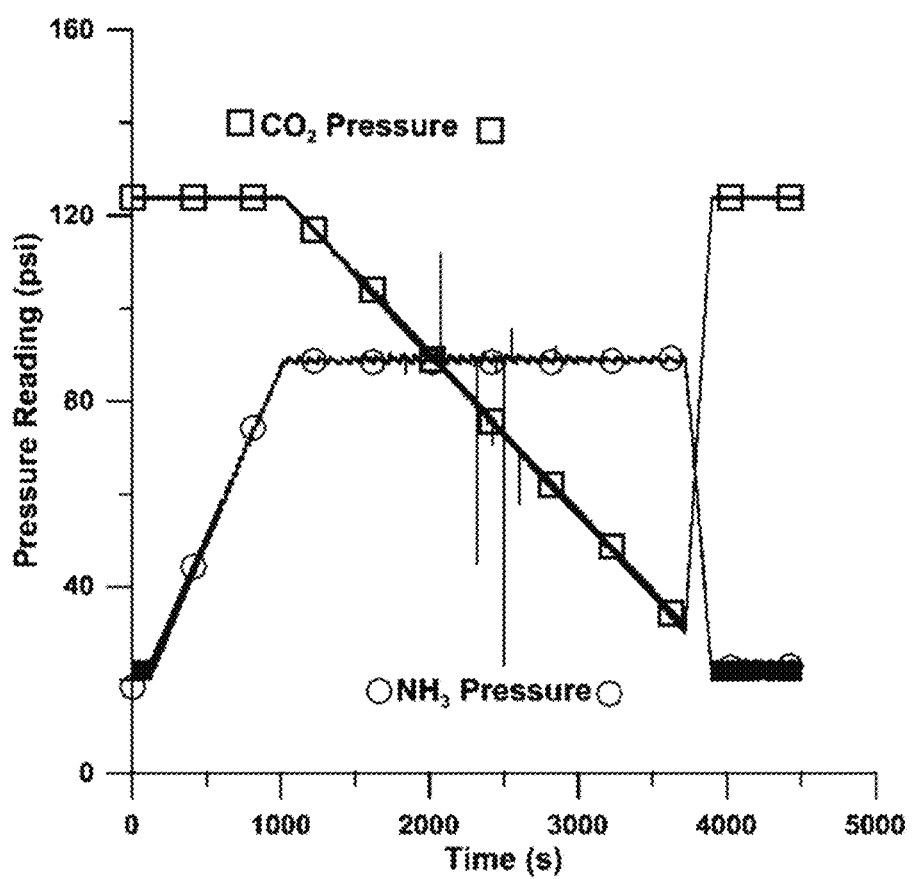
FIG. 33 is the gradient pressure readout used for the separation shown in FIG. 32. Separation starts with a low concentration of $NH_3$ and a high concentration of $CO_2$ to produce a low pH low ionic strength eluent. $NH_3$ pressure is first increased to increase the ionic strength followed by a reduction of $CO_2$ pressure to raise the pH. Spikes observed in the signal were due to electronic noise caused by valve actuation.

A pH separation of a monoclonal antibody lysate is shown in (FIG. 32) using a Thermo Scientific™ Dionex™ MAb-Pac™ SCX-10 2 mm column. Column effluent was monitored by UV absorbance detection. The separation is in good agreement with that provided as reference (FIG. 31). The gradient is shown in FIG. 33. A large peak eluting at 60 minutes is caused by the gradient transition to $CO_3^{2-}$ from $HCO_3^-$. Longer monitoring wavelengths don't show this peak as prominently but are less sensitive to the monoclonal antibody. The concentration used was 0.5 mg/mL.

3.7 Protein Separation

Figure 35:
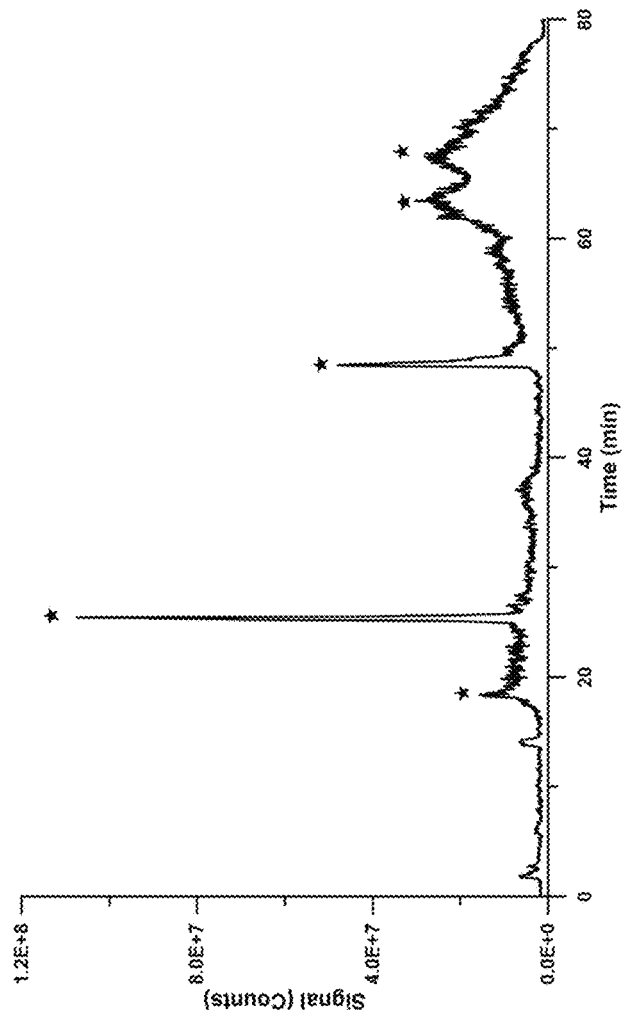
FIG. 35 shows separation of five proteins—Total Ion Chromatogram in the m/z 500-1500 range the protein peaks are indicated with an asterisk. Flow Rate 0.2 mL/min; Injection volume=10 µL; 1 mg/mL each Lactalbumin, Ubiquitine, Myoglobin, Cytochrome C (Bovine), Cytochrome C (Equine); 20 mM Formic Acid; Thermo Scientific™ Dionex™ MAbPac™ SCX-10. Proteins are eluted in their listed order. In the subsequent figures the mass spectra acquired for the asterisked peaks are provided. The elution order is governed by the pH of the solution except for the 2 cytochrome C proteins which are separated based on affinity for the column.
Figure 36:
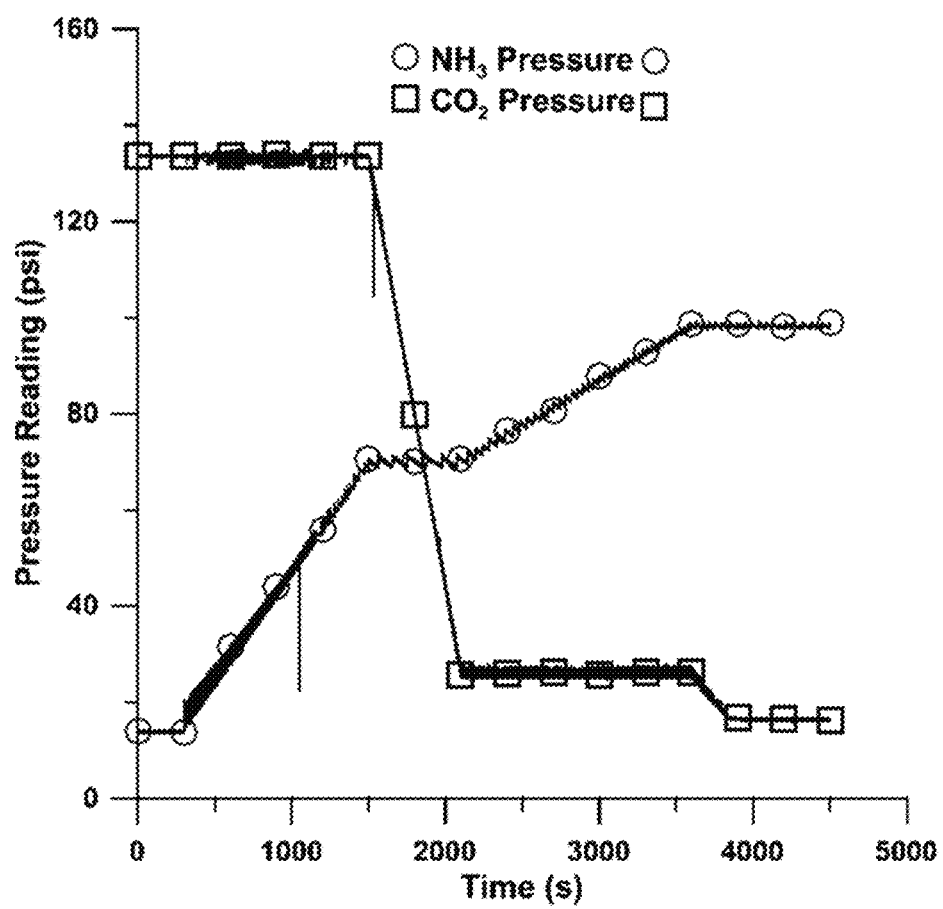
FIG. 36 shows the gradient pressure readout for the separation of 5 proteins shown in FIG. 35.
Figure 37:
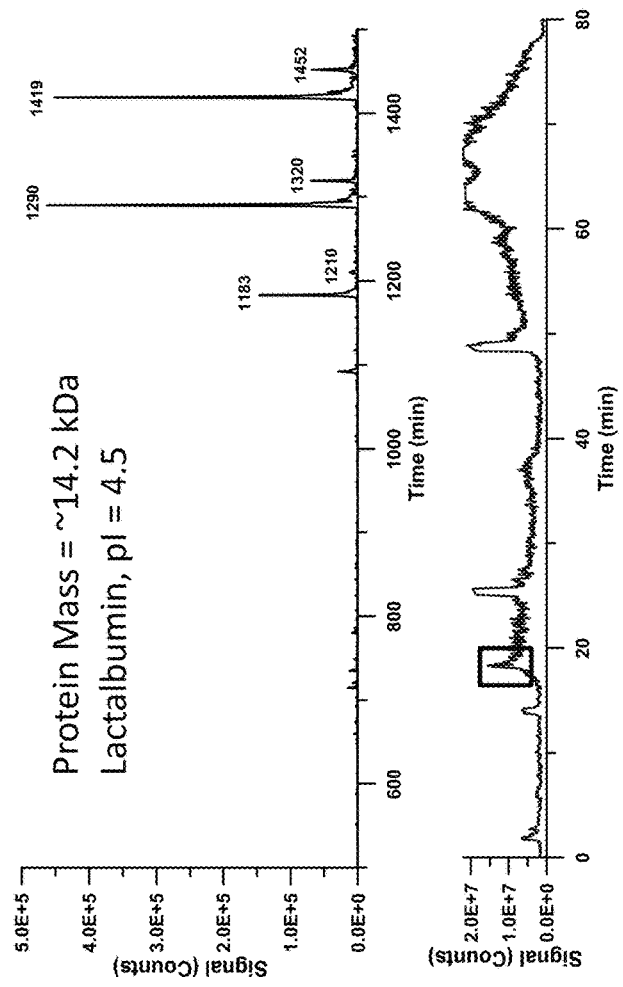
FIG. 37 shows the mass spectrum for the Lactalbumin peak eluting around 18 minutes. Thermo Scientific™ Dionex™ MAbPac™ SCX-10; Flow Rate 0.2 mL/min; Injection Volume Volume 10 µL; sample concentration 1 mg/mL; Engasser influent 20 mM Formic Acid.
Figure 38:
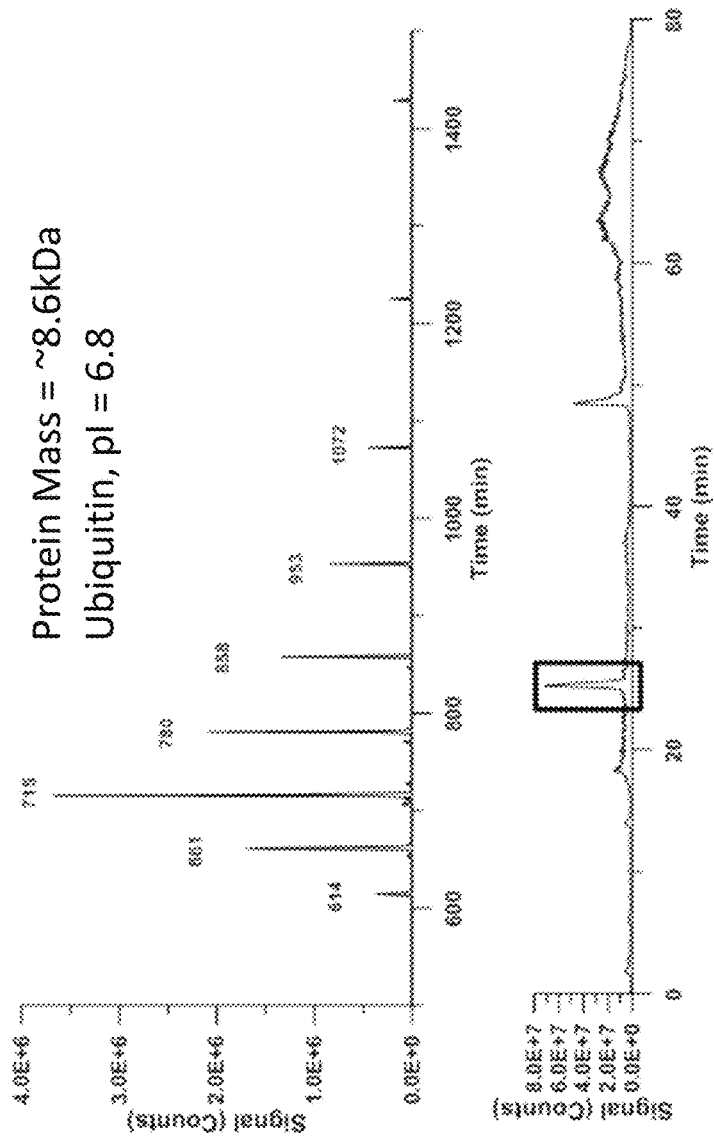
FIG. 38 shows the mass spectrum for the ubiquitin peak eluting around 25 minutes. Thermo Scientific™ Dionex™ MAbPac™ SCX-10; Flow Rate 0.2 mL/min; Injection Volume 10 µL; sample concentration 1 mg/mL; Engasser influent 20 mM Formic Acid.
Figure 39:
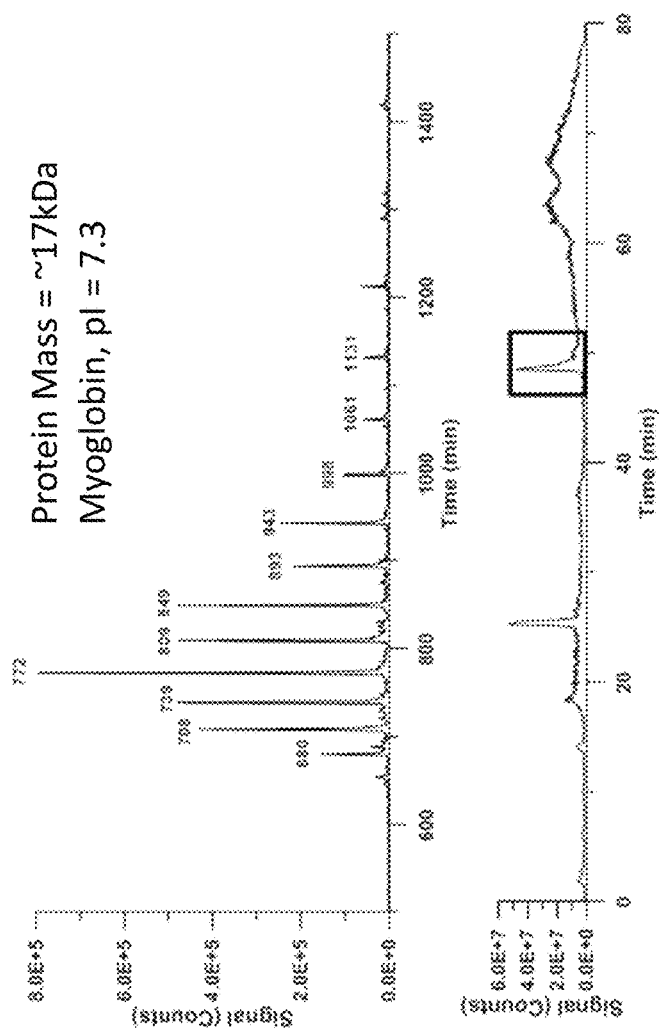
FIG. 39 shows the mass spectrum of the myoglobin peak eluting around 48 minutes. Thermo Scientific™ Dionex™ MAbPac™ SCX-10; Flow Rate 0.2 mL/min; Injection Volume 10 µL; sample concentration 1 mg/mL; Engasser influent 20 mM Formic Acid.
Figure 40:
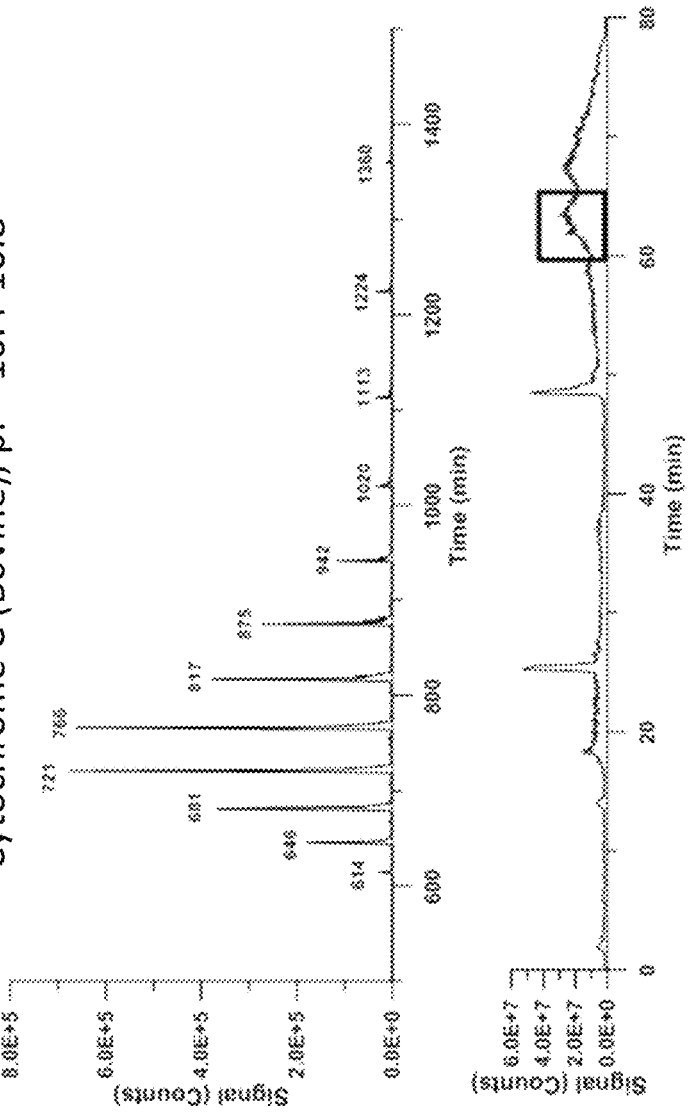
FIG. 40 shows the mass spectrum of the cytochrome c (bovine) peak eluting around 63 minutes. Thermo Scientific™ Dionex™ MAbPac™ SCX-10; Flow Rate 0.2 mL/min; Injection Volume 10 µL; sample concentration 1 mg/mL; Engasser influent 20 mM Formic Acid.
Figure 41:
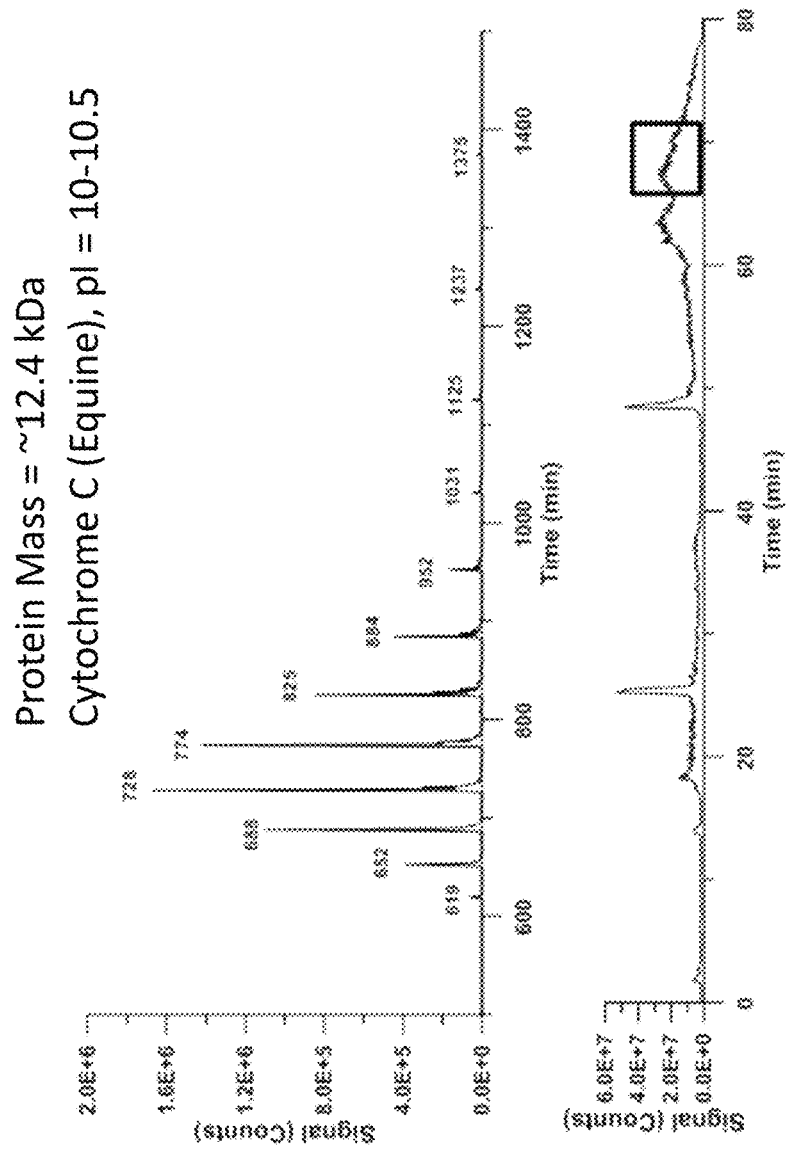
FIG. 41 shows the mass spectrum of the cytochrome c peak (equine) peak eluting around 67 minutes. Thermo Scientific™ Dionex™ MAbPac™ SCX-10; Flow Rate 0.2 mL/min; Injection Volume 10 µL; sample concentration 1 mg/mL; Engasser influent 20 mM Formic Acid.

A separation of 5 proteins was also performed using a pH gradient on the Thermo Scientific™ Dionex™ MAbPac™ SCX-10 column. The proteins were Myoglobin, Cytochrome C, Bovine, Ubiquitin, Lactalbumin, and Cytochrome C (Equine). FIG. 34 provides reference molecular weights and isoelectric point (pI) values. The proteins eluted from the column (FIG. 35) in order of ascending pI values as the gradient (FIG. 36) pH was increased. The total ion chromatogram of scans of m/z 500-1500 is shown in FIG. 35. Spectra of the identified peaks are provided in FIG. 37-41. Protein identification based on molecular weight shows that the proteins are eluted in order of increasing pI with the exception of the cytochrome c proteins which have nearly identical pI but different affinities for the stationary phase.

What is claimed is:

1. A system for performing a chromatographic separation of an analyte, said system comprising:
    (a) an eluent generator comprising:
        (i) a housing configured to be pressurizable by gas, comprising an annular void defined by said housing, and a gas inlet for said gas and a gas outlet for said gas in fluid communication with said annular void;
        (ii) a membrane permeable to said gas defining an eluent flow channel disposed within said annular void, said eluent flow channel having an eluent precursor fluid inlet and an eluent outlet;
        (iii) a source of said gas in fluidic communication with said gas inlet;
        (iv) a source of said eluent precursor fluid; and
        (v) a member selected from a gas input solenoid in fluidic communication with said source of said gas and said gas inlet and interposed therebetween, a gas exhaust solenoid in fluidic communication with said gas outlet, and a combination thereof; and
    (b) a chromatography column disposed downstream of and in fluidic communication with said eluent outlet.

2. The system according to claim 1, wherein said member selected from said gas input solenoid, said gas exhaust solenoid and a combination thereof is controlled by a controller such that pressure of said gas within said eluent generator is controlled to a preselected pressure by said controller.

3. The system according to claim 1, further comprising a pump in fluidic communication with said eluent flow channel inlet and configured to supply said eluent precursor fluid thereto.

4. The system according to claim 1, wherein said membrane is configured to permit passage of said gas from said annular void into said eluent flow channel and prevent or retard passage of said eluent from said eluent flow channel into said annular void.

5. The system according to claim 1, wherein said gas permeable membrane is an amorphous fluoropolymer.

6. The system according to claim 1, wherein said eluent is an aqueous eluent and said eluent precursor fluid is an aqueous eluent precursor fluid.

7. The system according to claim 1, further comprising a heating device configured to heat at least a portion of said eluent generator, thereby maintaining said gas in a gaseous state.

8. The system according to claim 7, wherein said heater heats at least said gas input or a component thereof.

9. The system according to claim 1, further comprising a vacuum device in fluidic communication with said gas outlet.

10. A method of performing a chromatographic separation using a chromatographic system according comprising:
(a) an eluent generator, comprising:
  (i) a housing configured to be pressurizable by gas, comprising an annular void defined by said housing, and a gas inlet for said gas and a gas outlet for said gas in fluid communication with said annular void;
  (ii) a membrane permeable to said gas defining an eluent flow channel disposed within said annular void, said eluent flow channel having an eluent precursor fluid inlet and an eluent outlet;
  (iii) a source of said gas in fluidic communication with said gas inlet;
  (iv) a source of said eluent precursor fluid; and
(b) a chromatography column disposed downstream of and in fluidic communication with said eluent outlet, said method comprising:
  (a1) flowing said eluent precursor fluid through said eluent flow channel while said annular void is maintained under positive pressure of said gas, said positive pressure selected to be of a magnitude sufficient to cause said gas to cross said gas permeable membrane, dissolving in said eluent precursor fluid, thereby forming said eluent;
  (b1) passing said eluent from said eluent outlet into said chromatography column;
  (c1) contacting said chromatography column with said analyte, thereby performing said chromatographic separation of said analyte.

11. The method according to claim 10, wherein said eluent precursor fluid is deionized water.

12. The method according to claim 10, wherein said eluent precursor fluid is aqueous NaOH or KOH.

13. The method according to claim 11 or 12, wherein said gas is $CO_2$.

14. The method according to claim 10, wherein said gas is a member selected from ammonia, a gas derived from a volatile amine and a gas derived from a volatile acid.

15. The method according to claim 10, wherein said eluent format is an isocratic format or a gradient format.

16. The method according to claim 15, wherein said pressure of said gas is maintained constant in said isocratic format.

17. The method according to claim 15, wherein said pressure of said gas is varied in said gradient format.

18. The method according to claim 10, wherein said chromatographic separation is a modality which is a member selected from ion exclusion, ion exchange, chiral amine separation, amino acid separation, and protein separation, including monoclonal antibody separation.

19. The method according to claim 10, further comprising, prior to performing said separation, controlling said device to produce said eluent, wherein said eluent has a pre-determined composition, said controlling comprising:
(a) selecting said gas, and pre-determining;
  (i) pressure of said gas in said annular void;
  (ii) composition of said eluent precursor solution in said eluent flow channel; and
  (iii) flow rate of said eluent precursor solution through said eluent flow channel; and
(b) controlling said eluent generator such that;
  (i) said pressure of said gas in said annular void is maintained at the pre-determined pressure;
  (ii) said composition of said eluent precursor fluid is maintained at the predetermined composition; and
  (iii) said flow rate of said eluent precursor fluid in said eluent flow channel is maintained at the predetermined flow rate,
thereby producing said eluent having said pre-determined composition.

20. The method of claim 19, further comprising pre-determining a rate of reaction of said gas with said eluent precursor, thereby determining concentration of a reaction product resulting therefrom in said eluent.

21. The method of claim 19, further comprising pre-determining a rate of dissolution of said gas in said eluent precursor, thereby determining concentration of said gas in said eluent.

22. The method of claim 19, wherein a parameter selected from:
  (i) said pressure of said gas in said annular void;
  (ii) said composition of said eluent precursor fluid;
  (iii) said flow rate of said eluent precursor fluid in said eluent flow channel; and
  (iv) a combination thereof
is maintained for a pre-determined time after which it is varied, thereby producing said eluent in a gradient format.

23. The method according to claim 10, further comprising: outputting said eluent and said analyte from said chromatography column; evaporating said eluent; detecting said analyte with a detector, in which said detector comprises an evaporative type of detector selected from a corona aerosol detector, an evaporated light scattering detector, an electrospray ionization mass spectrometer, and a combination thereof.

24. The method according to claim 10, further comprising: outputting said eluent and said analyte from said chromatography column to a gas removal device; removing said gas with the gas removal device; detecting said analyte with a detector.

25. An eluent generator configured for generating an eluent of a pre-determined composition and for incorporation into a system for chromatographic separation of an analyte, said eluent generator comprising:
(a) a housing configured to be pressurizable by gas, comprising an annular void defined by said housing, and a gas inlet for said gas and a gas outlet for said gas in fluid communication with said annular void;
(b) a membrane permeable to said gas defining an eluent flow channel disposed within said annular void, said eluent flow channel having an eluent precursor fluid inlet and an eluent outlet, said outlet configured for coupling to a chromatography column and fluidically communicating therewith;
(c) a first solenoid communicating fluidically with said gas inlet and controlled by a first controller; and
(d) a second solenoid communicating fluidically with said gas outlet and controlled by a second controller,
wherein said first controller and said second controller are programmed to operate cooperatively to control pressure of said gas in said annular void at a pre-determined value, thereby generating said eluent of said pre-determined composition.

26. A system for performing a chromatographic separation of an analyte, said system comprising:
(a) an eluent generator comprising:
  (i) a housing configured to be pressurizable by gas, comprising an annular void defined by said housing, and a gas inlet for said gas and a gas outlet for said gas in fluid communication with said annular void;

(ii) a membrane permeable to said gas defining an eluent flow channel disposed within said annular void, said eluent flow channel having an eluent precursor fluid inlet and an eluent outlet;

(iii) a source of said gas in fluidic communication with said gas inlet, wherein said source of gas provides a gas selected from $CO_2$, a gas derived from a volatile acid, a gas derived from a volatile base, and ammonia;

(iv) a source of said eluent precursor fluid; and (b) a chromatography column disposed downstream of and in fluidic communication with said eluent outlet.

27. A system for performing a chromatographic separation of an analyte, said system comprising:

(a) an eluent generator comprising:

(i) a housing configured to be pressurizable by gas, comprising an annular void defined by said housing, and a gas inlet for said gas and a gas outlet for said gas in fluid communication with said annular void;

(ii) a membrane permeable to said gas defining an eluent flow channel disposed within said annular void, said eluent flow channel having an eluent precursor fluid inlet and an eluent outlet;

(iii) a source of said gas in fluidic communication with said gas inlet;

(iv) a source of said eluent precursor fluid;

(b) a chromatography column disposed downstream of and in fluidic communication with said eluent outlet; and (c) a delay device in fluidic communication with said eluent outlet and said chromatography column and interposed therebetween, said delay device configured to retard flow of said eluent to said chromatography column and promote dissolution of said gas into said eluent prior to said eluent flowing to said chromatography column.

28. A system for performing a chromatographic separation of an analyte, said system comprising:

(a) an eluent generator comprising:

(i) a housing configured to be pressurizable by gas, comprising an annular void defined by said housing, and a gas inlet for said gas and a gas outlet for said gas in fluid communication with said annular void;

(ii) a membrane permeable to said gas defining an eluent flow channel disposed within said annular void, said eluent flow channel having an eluent precursor fluid inlet and an eluent outlet;

(iii) a source of said gas in fluidic communication with said gas inlet;

(iv) a source of said eluent precursor fluid; and (b) a chromatography column disposed downstream of and in fluidic communication with said eluent outlet; and (c) a suppressor configured to suppress ions of said eluent, said suppressor disposed downstream of said chromatography column and in fluidic communication therewith.

29. A system for performing a chromatographic separation of an analyte, said system comprising:

(a) an eluent generator comprising:

(i) a housing configured to be pressurizable by gas, comprising an annular void defined by said housing, and a gas inlet for said gas and a gas outlet for said gas in fluid communication with said annular void;

(ii) a membrane permeable to said gas defining an eluent flow channel disposed within said annular void, said eluent flow channel having an eluent precursor fluid inlet and an eluent outlet;

(iii) a source of said gas in fluidic communication with said gas inlet;

(iv) a source of said eluent precursor fluid;

(b) a chromatography column disposed downstream of and in fluidic communication with said eluent outlet; and (c) a gas removal device disposed in between said chromatography column and a detector, wherein said detector is configured to detect at least one component of said analyte, said detector disposed downstream of said chromatography column and in fluidic communication therewith.

30. The system according to claim 29, in which said detector comprises an evaporative type of detector selected from a corona charged aerosol detector, an evaporative light scattering detector, an electrospray ionization mass spectrometer, and a combination thereof.

* * * * *